United States Patent
Rosenberg et al.

(10) Patent No.: US 11,707,420 B2
(45) Date of Patent: Jul. 25, 2023

(54) COMPOSITIONS, KITS, AND METHODS FOR ALTERING THE COLOR OF HAIR

(71) Applicant: L'Oreal, Paris (FR)

(72) Inventors: Marc Philip Rosenberg, Westfield, NJ (US); Leslie A. Warner, Jersey City, NJ (US); Wonhee Allison Park, Teaneck, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 17/899,079

(22) Filed: Aug. 30, 2022

(65) Prior Publication Data

US 2023/0097564 A1 Mar. 30, 2023

Related U.S. Application Data

(60) Provisional application No. 63/239,276, filed on Aug. 31, 2021.

(30) Foreign Application Priority Data

Oct. 19, 2021 (FR) ...................................... 2111066

(51) Int. Cl.
| | |
|---|---|
| *A61Q 5/10* | (2006.01) |
| *A61K 8/06* | (2006.01) |
| *A61K 8/39* | (2006.01) |
| *A61K 8/34* | (2006.01) |
| *A61K 8/41* | (2006.01) |
| *A61K 8/22* | (2006.01) |
| *A61K 8/36* | (2006.01) |

(52) U.S. Cl.
CPC ................. *A61K 8/06* (2013.01); *A61K 8/22* (2013.01); *A61K 8/342* (2013.01); *A61K 8/361* (2013.01); *A61K 8/39* (2013.01); *A61K 8/41* (2013.01); *A61Q 5/10* (2013.01); *A61K 2800/432* (2013.01)

(58) Field of Classification Search
CPC . A61K 8/06; A61K 8/22; A61K 8/342; A61K 8/361; A61K 8/39; A61K 8/41; A61K 2800/432; A61Q 5/10
USPC ........................................................... 8/405
See application file for complete search history.

(56) References Cited

U.S. PATENT DOCUMENTS

| | | | |
|---|---|---|---|
| 3,915,921 A | 10/1975 | Schlatzer, Jr. | |
| 4,003,699 A | 1/1977 | Rose et al. | |
| RE30,199 E | 1/1980 | Rose et al. | |
| 4,509,949 A | 4/1985 | Huang et al. | |
| 5,061,289 A | 10/1991 | Clausen et al. | |
| 5,380,340 A | 1/1995 | Neunhoeffer et al. | |
| 5,534,267 A | 7/1996 | Neunhoeffer et al. | |
| 5,645,609 A | 7/1997 | Andrean et al. | |
| 5,663,366 A | 9/1997 | Neunhoeffer et al. | |
| 5,707,151 A | 1/1998 | Parker et al. | |
| 5,766,576 A | 6/1998 | Löwe et al. | |
| 6,099,592 A | 8/2000 | Vidal et al. | |
| 6,284,003 B1 | 9/2001 | Rose et al. | |
| 6,730,789 B1 | 5/2004 | Birault et al. | |
| 7,115,147 B2 | 10/2006 | Desenne et al. | |
| 7,223,294 B2 | 5/2007 | Desenne et al. | |
| 8,241,370 B2 | 8/2012 | Legrand et al. | |
| 10,434,042 B2 * | 10/2019 | Tsuzuki | A61K 8/342 |
| 2010/0242187 A1 * | 9/2010 | Miyabe | A61K 8/342 8/406 |
| 2010/0257677 A1 * | 10/2010 | Miyabe | A61K 8/463 8/405 |
| 2011/0150797 A1 * | 6/2011 | Legrand | A61K 8/19 8/408 |
| 2017/0035667 A1 * | 2/2017 | Benn | A61K 8/41 |
| 2019/0201309 A1 * | 7/2019 | Machover | A61Q 5/10 |

FOREIGN PATENT DOCUMENTS

| | | | |
|---|---|---|---|
| DE | 2359399 A1 | 6/1975 | |
| DE | 3843892 A1 | 6/1990 | |
| DE | 4133957 A1 | 4/1993 | |
| DE | 19543988 A1 | 5/1997 | |
| EP | 0080976 A1 | 6/1983 | |
| EP | 0714954 A2 | 6/1996 | |
| EP | 0770375 A1 | 5/1997 | |
| EP | 2204158 A1 | 7/2010 | |
| EP | 22041158 A1 * | 7/2010 | |
| FR | 1462788 A | 12/1966 | |
| FR | 2679771 A1 | 2/1993 | |
| FR | 2733749 A1 | 11/1996 | |
| FR | 2801308 A1 | 5/2001 | |
| FR | 2886136 A1 | 12/2006 | |
| FR | 2925304 A1 | 6/2009 | |
| FR | 29253304 A1 * | 6/2009 | |
| FR | 2968946 A1 | 6/2012 | |
| FR | 3082119 A1 * | 12/2019 | |

(Continued)

OTHER PUBLICATIONS

International Search Report and Written Opinion for counterpart Application No. PCT/US2022/042169, dated Jan. 23, 2023.
Todd, Charles, et al., "Volatile Silicone Fluids for Cosmetic Formulations," Cosmetics and Toiletries, vol. 91, Jan. 1976, pp. 29-32.
French Preliminary Search Report and Written Opinion for FR Application No. 2111066, dated Jun. 27, 2022.

*Primary Examiner* — Eisa B Elhilo
(74) *Attorney, Agent, or Firm* — The Marbury Law Group, PLLC

(57) ABSTRACT

The disclosure relates to hair color base compositions comprising an alkoxylated fatty alcohol, a fatty acid, a fatty alcohol, a buffer system, and optionally a thickening agent and/or colorant compound, hair color altering compositions comprising the hair color base, and kits and methods for altering the color of keratinous fibers such as hair.

21 Claims, No Drawings

(56) References Cited

FOREIGN PATENT DOCUMENTS

| | | |
|---|---|---|
| GB | 1026978 A | 4/1966 |
| GB | 1124911 A | 8/1968 |
| GB | 1153196 A | 5/1969 |
| JP | 02-019576 A | 1/1990 |
| JP | 05-163124 A | 6/1993 |
| WO | 94/08969 A1 | 4/1994 |
| WO | 94/08970 A1 | 4/1994 |
| WO | 95/01772 A1 | 1/1995 |
| WO | 95/15144 A1 | 6/1995 |
| WO | 96/15765 A1 | 5/1996 |
| WO | 2012/084473 A1 | 6/2012 |
| WO | 2017/024261 A1 | 2/2017 |
| WO | WO 2017024261 A1 * | 2/2017 |
| WO | 2019/002072 A1 | 1/2019 |
| WO | WO 2019/234193 A1 * | 12/2019 ............... A61Q 5/10 |

\* cited by examiner

COMPOSITIONS, KITS, AND METHODS FOR ALTERING THE COLOR OF HAIR

CROSS REFERENCE TO RELATED APPLICATIONS

This application claims priority to U.S. Provisional Patent Application No. 63/239,276, filed Aug. 31, 2021, and FR 2111066 filed Oct. 19, 2021, both of which are incorporated by reference herein in their entireties.

TECHNICAL FIELD

The present disclosure relates to a hair color base in the form of an emulsion or cream comprising an alkoxylated fatty alcohol, a fatty acid, a fatty alcohol other than the alkoxylated fatty alcohol, a buffer system, and optionally a thickening agent and/or colorant compound, hair color altering compositions comprising the hair color base, and kits and methods for altering the color of hair.

BACKGROUND

Changing or enhancing the appearance of hair is very popular with consumers, including for example changing hair color and/or imparting various properties, for example, shine and conditioning of the hair. Hair coloring typically involves bleaching, lightening, and/or changing the hair color through oxidative dyes, direct dyes, and/or pigments providing a different shade or color, and/or lifting the color of the hair.

Hair lightening processes, or lifting the color of hair, generally require the use of compositions that comprise at least one oxidizing agent to lighten the color of dark hair to lighter shades. When colorants or dye compounds such as oxidation dye precursors and/or direct dyes are present in these compositions, such compositions can change or deposit color while lightening the color of hair at the same time. Conventional hair coloring products are permanent dye compositions comprising oxidation dye precursors, which are also known as primary intermediates or couplers. These oxidation dye precursors are colorless or weakly colored compounds which, when combined with oxidizing agents, give rise to colored complexes by a process of oxidative condensation.

Variation in tone height before and after the application of a hair color-altering composition is typically evaluated when lightening or lifting the color of the hair. The degree or level of lightening or lift is determined by the variation. "Tone" refers to the "finish" of a shade, including is degree of warmth or coolness and is based on the classification of natural shades, one tone separating each shade from the shade immediately following or preceding it. Tone heights or levels typically range from 1 (black) to 10 (light blonde), one unit generally corresponding to one tone. Accordingly, the higher the tone number, the lighter the shade and the greater the degree of lift.

Hair lightening or color lifting compositions may require at least one alkalizing agent, such as ammonia, an ammonia gas-generating compound, an amine, and/or ammonium-based compound. The alkalizing agent causes the hair shaft to swell, thus allowing small oxidative dye molecules to penetrate the cuticle and cortex before the oxidation condensation process is completed. The resulting larger-sized colored complexes from the oxidative reaction are then trapped inside the hair fiber, thereby permanently altering the color of the hair. While such hair dyeing and/or color lifting compositions can effectively alter the color of hair, these compositions can damage the hair fibers and/or irritate the scalp due to excessively high levels of alkalinity.

Such damage and/or irritation can be exacerbated by processing time. Typical processing times can range from thirty (30) minutes to as much as forty-five (45) or sixty (60) minutes or more. The greater the processing time, the lighter the hair result and/or the more intense the color application. However, as the processing time increases, typically more damage to the hair and/or irritation to the scalp results. There is, therefore, a need for compositions and methods that can lift the color of hair and/or deposit color onto hair in an efficient and/or improved manner, while preventing excess damage to the hair and/or scalp irritation.

Use of new and additional ingredients and novel combinations of ingredients are continuously sought in attempts to mitigate or avoid hair damage and/or scalp irritation, as well as to improve the cosmetic performance of hair color lifting and hair dyeing compositions. While achieving desired safety and performance objectives, however, the choice of ingredients or combinations of ingredients frequently pose difficulties insofar as they cannot be detrimental to other cosmetic attributes. Ingredient combinations must be considered for attributes such as, ease and uniformity of application, rheology or viscosity properties, stability of the compositions, and/or color deposit and target shade formation, while weighing potential disadvantages such as increased damage and/or a less healthy look to the hair.

Thus, an objective of the present disclosure is to provide novel emulsion or cream hair color base compositions for altering the color of hair by lifting or lightening the color of the hair, and depositing color onto the hair, that require less processing time thereby minimizing the damage to the hair and overall minimizing other adverse effects.

SUMMARY

The present disclosure relates to compositions and methods for altering the color of hair using a buffer system that provides reduced processing times in methods for altering the color of the hair. While typical processing times are in the range of thirty minutes to forty-five minutes, processing times of the subject compositions and methods are significantly reduced, ranging from about five to twenty minutes. As a result, the subject compositions and methods avoid and/or mitigate damage of the hair and/or scalp during lightening of the hair while at the same time, providing a much more efficient, faster processing time. In various embodiments, the compositions and methods described nevertheless allow one to achieve a desired level of color lift in tone within the reduced processing times. In further embodiments, the compositions and methods allow one to additionally deposit color onto hair within the reduced processing times.

In some embodiments, the disclosure relates to a hair color base in the form of a cream or an emulsion comprising: (a) about 10% to about 30% of alkoxylated fatty alcohols; (b) about 1% to about 8% of fatty acids; (c) at least about 8% of fatty alcohols other than alkoxylated fatty alcohols; and (d) a buffer system comprising: (i) about 0.1% to about 10% ammonium hydroxide; (ii) about 0.1% to about 5% ammonium bicarbonate; and (iii) optionally, about 0.5% to about 5% of monoethanolamine, wherein the molar ratio of ammonium hydroxide to ammonium bicarbonate is at least about 1.5, for example from about 1.5 to about 4, for example from about 1.5 to about 2, and all amounts are by weight, based on the total weight of the hair color base. Optionally, the hair color base may comprise additional components, for example thickeners and colorant compounds. In some embodiments, the colorant compounds are oxidation dye precursors, and are present in the hair color base in an amount of about 0.5% to about 5%. In some embodiments, the molar ratio of ammonium hydroxide to ammonium bicarbonate is about 1.75. The disclosure further relates to hair color altering compositions comprising an oxidizing component, e.g. hydrogen peroxide, and the hair color base.

In further embodiments, the disclosure relates to a hair color base in the form of a cream or an emulsion comprising: (a) about 15% to about 25% of alkoxylated fatty alcohols; (b) about 2% to about 6% of fatty acids; (c) about 8% to about 15% of fatty alcohols other than alkoxylated fatty alcohols; (d) a buffer system comprising: (i) about 2% to about 6%, for example about 3.5% to about 4.25%, of ammonium hydroxide; (ii) about 0.25% to about 2.5%, for example about 0.5% to about 1.5%, of ammonium bicarbonate; and (iii) optionally, about 0.5% to about 2.5%, for example about 0.5% to about 1.5%, of monoethanolamine; (e) at least one oxidation dye precursor; (f) and at least one thickening agent, wherein the molar ratio of ammonium hydroxide to ammonium bicarbonate ranges from about 1.5 to about 4, preferably about 1.5 to about 2, for example about 1.75, and all amounts are by weight, based on the total weight of the hair color base. The disclosure further relates to hair color altering compositions comprising an oxidizing component, e.g. hydrogen peroxide, and the hair color base.

The disclosure also relates to hair color altering compositions comprising an oxidizing component, e.g. hydrogen peroxide, and a hair color base comprising: (a) about 10% to about 30% of alkoxylated fatty alcohols; (b) about 1% to about 8% of fatty acids; (c) at least about 10% of fatty alcohols other than alkoxylated fatty alcohols; (d) a buffer system comprising: (i) about 0.1% to about 10%, for example about 1% to about 6%, of ammonium hydroxide; (ii) about 0.1% to about 5%, for example about 0.25% to about 2.5%, of ammonium bicarbonate; and (iii) optionally, about 0.5% to about 5%, for example about 0.5% to about 2.5%, of monoethanolamine; (e) at least one oxidation dye precursor; and (f) at least one thickening agent, wherein the molar ratio of ammonium hydroxide to ammonium bicarbonate is at least about 1.5, for example about 1.5 to about 4, preferably about 1.5 to about 2, or is about 1.75, wherein all amounts are by weight, based on the total weight of the hair color base.

In further embodiments, the disclosure relates to a hair color altering composition comprising: an oxidizing agent, e.g. hydrogen peroxide; about 5% to about 15% of alkoxylated fatty alcohols; about 0.5% to about 4% of fatty acids; at least about 5% of fatty alcohols other than alkoxylated fatty alcohols; about 0.05% to about 5%, for example about 1% to about 2.5%, of ammonium hydroxide; about 0.05% to about 2.5%, for example about 0.25% to about 1%, of ammonium bicarbonate; optionally about 0.25% to about 2.5%, for example about 0.25% to about 1%, of monoethanolamine; optionally at least one oxidation dye precursor; and optionally at least one thickening agent, wherein the molar ratio of ammonium hydroxide to ammonium bicarbonate is at least about 1.5, for example about 1.5 to about 4, preferably about 1.5 to about 2, or is about 1.75, wherein all amounts are by weight, based on the total weight of the hair color altering composition.

The disclosure also relates to methods of altering the color of keratin fibers by applying the hair color altering compositions according to the disclosure to the keratin fibers, in particular hair such as human hair. In various embodiments, the hair color altering compositions are not left on the hair for a period of time greater than about 25 minutes, for example not greater than about 20 minutes, or not greater than about 15 minutes. In a preferred embodiment, the hair color altering compositions are not left on the hair for a period of time greater than about 10 minutes. Thus, the hair color altering compositions may be removed, e.g. rinsed, from the hair after a period of about 10 to about 15 minutes, or after about 10 minutes.

The disclosure also relates to kits comprising the hair color base according to the disclosure in a first compartment or container, and comprising an oxidizing component in a second compartment or container.

DETAILED DESCRIPTION

It has been surprisingly and unexpectedly discovered that a hair color base in the form of an emulsion or cream and comprising a buffer system according to the disclosure significantly decreases processing time for hair lightening and/or coloring treatments, thereby minimizing the amount of time hair is exposed to the lightening/coloring treatment and thus minimizing damage to the hair. The emulsion or cream hair color base and buffer system provide the performance of a traditional (e.g. 30-45 minutes) permanent cream color process in less than about 25 minutes, for example less than about 20 minutes or less than about 15 minutes, such as in about 10 minutes. Advantageously, such hair color base compositions avoid or reduce the risk of over-processing due to their reduced processing time. At the same time, the disclosed emulsion or cream hair color composition with buffer systems used with lightening/hair coloring treatments was found to improve hair color, lightening, and/or lifting effects in the decreased processing time. For example, the composition provides good uniformity of lift along the fiber between the tip and the root of the hair (also called the "selectivity" of lightening), while decreased processing time mitigates damage to the hair and/or scalp.

Thus, the present disclosure relates to emulsion or cream hair color base compositions comprising an alkoxylated fatty alcohol, a fatty acid, a fatty alcohol, a buffer system, and optionally a thickening agent and/or colorant compound, and to compositions for altering the color of the hair comprising the emulsion or cream hair color base. Kits and methods of altering the color of the hair are also disclosed.

Hair Color Base

Hair color bases according to the disclosure can be used in compositions and methods for altering the color of the hair. The hair color bases according to the disclosure are in the form of an emulsion or cream, and comprise at least one alkoxylated fatty alcohol, at least one fatty acid, at least one fatty alcohol, a buffer system, and optionally other components useful in compositions for altering the color of the hair, for example at least one thickening agent and/or at least one colorant compound.

Alkoxylated Fatty Alcohols

The hair color base compositions comprise at least one alkoxylated fatty alcohol. In various embodiments, the alkyl chain may be in the $C_{12}$-$C_{50}$ range, for example in the $C_{16}$-$C_{40}$ range, or in the $C_{24}$ to $C_{40}$ range, and may have from about 1 to about 110 alkoxy groups. The alkoxy groups may, in various embodiments, be chosen from $C_2$-$C_6$ oxides and their mixtures, with ethylene oxide, propylene oxide, and their mixtures being useful examples. The alkyl chain may be linear, branched, saturated, or unsaturated. In some embodiments, the fatty alcohol component comprises, consists essentially of, or consists of ethoxylated and/or propoxylated fatty alcohols.

Non-limiting examples of useful alkoxylated fatty alcohols include ceteareth-2, ceteareth-3, ceteareth-4, ceteareth-5, ceteareth-6, ceteareth-7, ceteareth-8, ceteareth-9, ceteareth-10, ceteareth-11, ceteareth-12, ceteareth-13, ceteareth-14, ceteareth-15, ceteareth-16, ceteareth-17, ceteareth-18, ceteareth-20, ceteareth-22, ceteareth-23, ceteareth-24, ceteareth-25, ceteareth-27, ceteareth-28, ceteareth-29, ceteareth-30, ceteareth-33, ceteareth-34, ceteareth-40, ceteareth-50, ceteareth-55, ceteareth-60, ceteareth-80, ceteareth-100, laureth-1, laureth-2, laureth-3, laureth-4, laureth-5, laureth-6, laureth-7, laureth-8, laureth-9, laureth-10, laureth-11, laureth-12, laureth-13, laureth-14, laureth-15, laureth-16, laureth-20, laureth-23, laureth-25, laureth-30, laureth-40, deceth-3, deceth-5, oleth-5, oleth-30, steareth-2, steareth-10, steareth-20, steareth-100, cetylsteareth-12, ceteareth-5, ceteareth-5, polyglyceryl 4-lauryl ether, polyglyceryl 4-oleyl ether, polyglyceryl 2-oleyl ether, polyglyceryl 2-cetyl ether, polyglyceryl 6-cetyl ether, polyglyceryl 6-oleylcetyl ether, polyglyceryl 6-octadecyl ether, C9-C11 pareth-3, C9-C11 pareth-6, C11-C15 pareth-3, C11-C15 pareth-5, C11-C15 pareth-12, C11-C15 pareth-20, C12-C15 pareth-9, C12-C15 pareth-12, and C22-C24 pareth-33.

In certain embodiments, the at least one alkoxylated fatty alcohol is chosen from laureth-3 (a lauryl ethoxylate having an average degree of ethoxylation of 3), laureth-12 (a lauryl ethoxylate having an average degree of ethoxylation of 12), laureth-23 (a lauryl ethoxylate having an average degree of ethoxylation of 23), ceteth-10 (a cetyl alcohol ethoxylate having an average degree of ethoxylation of 10) steareth-10 (a stearyl alcohol ethoxylate having an average degree of ethoxylation of 10), and steareth-2 (a stearyl alcohol ethoxylate having an average degree of ethoxylation of 2), steareth-20 (a stearyl alcohol ethoxylate having an average degree of ethoxylation of 20), steareth-100 (a stearyl alcohol ethoxylate having an average degree of ethoxylation of 100), beheneth-5 (a behenyl alcohol ethoxylate having an average degree of ethoxylation of 5), beheneth-10 (a behenyl alcohol ethoxylate having an average degree of ethoxylation of 10), or mixtures thereof. In various embodiments, the at least one alkoxylated fatty alcohol comprises, consists essentially of, or consists of deceth-3, oleth-30, laureth-12, or mixtures thereof.

The alkoxylated fatty alcohols are generally present in the hair color base compositions in an amount ranging from about 10% to about 30% by weight, relative to the total weight of the hair color base composition. For example, in various embodiments, the hair color base compositions comprise from about 10% to about 28%, about 10% to about 25%, about 10% to about 22%, about 12% to about 30%, about 12% to about 28%, about 12% to about 25%, about 12% to about 22%, about 15% to about 30%, about 15% to about 28%, about 15% to about 25%, about 15% to about 22%, about 18% to about 30%, about 18% to about 28%, about 18% to about 25%, or about 18% to about 22% by weight of alkoxylated fatty alcohols, based on the total weight of the hair color base composition.

Fatty Acids

The hair color base compositions comprise at least one fatty acid. In various exemplary and non-limiting embodiments, the fatty acids contain from 6 to 22 carbon atoms, for example from 8 to 20 carbon atoms, or from 10 to 18 carbon atoms. Exemplary and non-limiting fatty acids include oleic acid, stearic acid, isostearic acid, lauric acid, palmitic acid, myristic acid, linoleic acid, capric acid and caprylic acid, or mixtures thereof.

Esters of fatty acids, such as those listed above, may also be used. Exemplary fatty acid esters include esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total number of carbons of the esters being, for example, greater than or equal to 10.

Among the monoesters, non-limiting examples include dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso) stearyl octanoate; isocetyl octanoate; octyl octanoate; cetyl octanoate; decyl oleate; glycol distearate; isocetyl isostearate; isocetyl laurate; isocetyl stearate; isodecyl octanoate; isodecyl oleate; isononyl isononanoate; isostearyl palmitate; methyl acetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, ethyl-2-hexyl palmitate, 2-octyldecyl palmitate, alkyl myristates such as isopropyl, butyl, cetyl, 2-octyldodecyl, mirystyl, stearyl myristate, hexyl stearate, butyl stearate, isobutyl stearate; dioctyl malate, hexyl laurate, and 2-hexyldecyl laurate.

In some embodiments, glyceryl esters and polyglyceryl esters of fatty acids, including but not limited to glyceryl monoesters, such as glyceryl monoesters of $C_{16}$-$C_{22}$ saturated or unsaturated, linear or branched chain fatty acids such as glyceryl oleate, glyceryl monostearate, glyceryl monoisostearate, glyceryl monopalmitate, glyceryl monobehenate, or mixtures thereof, and polyglyceryl esters of $C_{16}$-$C_{22}$ saturated or unsaturated, linear or branched chain fatty acids, such as polyglyceryl-4 isostearate, polyglyceryl-3 oleate, polyglyceryl-2 sesquioleate, triglyceryl diisostearate, diglyceryl monooleate, tetraglyceryl monooleate, or mixtures thereof may be chosen.

Sorbitan esters of fatty acids, for example of $C_{16}$-$C_{22}$ saturated or unsaturated, linear or branched chain fatty acids, may also be used. Representative and non-limiting examples of suitable sorbitan esters include sorbitan monooleate (e.g., SPAN® 80), sorbitan sesquioleate (e.g., Arlacel® 83 from Croda, Inc., Edison, N.J.), sorbitan monoisostearate (e.g., CRILL® 6 from Croda, Inc., Edison, N.J.), sorbitan stearates (e.g., SPAN® 60), sorbitan trioleate (e.g., SPAN® 85), sorbitan tristearate (e.g., SPAN® 65), sorbitan dipalmitates (e.g., SPAN® 40), and sorbitan isostearate.

The fatty acids are generally present in the hair color base compositions in an amount ranging from about 1% to about 8% by weight, relative to the total weight of the hair color base composition. For example, in various embodiments, the hair color base compositions comprise from about 1% to about 7%, about 1% to about 6%, about 1% to about 5%, about 1% to about 4%, about 1% to about 3%, about 1% to about 2%, about 2% to about 8%, about 2% to about 7%, about 2% to about 6%, about 2% to about 5%, about 2% to about 4%, about 2% to about 3%, about 3% to about 8%, about 3% to about 7%, about 3% to about 6%, about 3% to about 5%, about 3% to about 4%, about 4% to about 8%, about 4% to about 7%, about 4% to about 6%, or about 4% to about 5% by weight of fatty acids, based on the total weight of the hair color base composition.

Fatty Alcohols

The hair color base compositions comprise at least one fatty alcohol other than the alkoxylated fatty alcohol. For example, in various exemplary and non-limiting embodiments, the fatty alcohol may be a non-alkoxylated, saturated or unsaturated, linear or branched fatty alcohol having from 6 to 30 carbon atoms, such as from 8 to 30 carbon atoms. As non-limiting examples, cetyl alcohol, stearyl alcohol and their mixture (cetearyl alcohol), octyldodecanol, 2-butyloctanol, 2-hexyldecanol, 2-undecylpentadecanol, oleic alcohol, linoleic alcohol, or mixtures thereof may be chosen.

In further embodiments, at least one fatty alcohol may be chosen from C9-C11 alcohols, C12-C13 alcohols, C12-C15 alcohols, C12-C16 alcohols, or C14-C15 alcohols. Optionally, the at least one fatty alcohol may be chosen from arachidyl alcohol, behenyl alcohol, caprylic alcohol, cetearyl alcohol, cetyl alcohol, coconut alcohol, decyl alcohol, hydrogenated tallow alcohol, jojoba alcohol, lauryl alcohol, myristyl alcohol, oleyl alcohol, palm alcohol, palm kernel alcohol, stearyl alcohol, tallow alcohol, tridecyl alcohol, or mixtures thereof. In at least some embodiments, the at least one fatty alcohol comprises, consists essentially of, or consists of cetearyl alcohol.

The fatty alcohols are generally present in the hair color base compositions in an amount of at least about 8%, for example at least about 9% or at least about 10% by weight, relative to the total weight of the hair color base composition. For example, in various embodiments, the hair color base compositions comprise from about 8% to about 20%, about 8% to about 18%, about 8% to about 15%, about 8% to about 13%, about 8% to about 12%, about 9% to about 20%, about 9% to about 18%, about 9% to about 15%, about 9% to about 13%, about 9% to about 12%, about 10% to about 20%, about 10% to about 18%, about 10% to about 15%, about 10% to about 13%, about 10% to about 12%, about 11% to about 20%, about 11% to about 18%, about 11% to about 15%, about 11% to about 13%, or about 11% to about 12% by weight of fatty alcohols other than the alkoxylated fatty alcohol, based on the total weight of the hair color base composition.

Buffer System

The buffer system comprises ammonium hydroxide, ammonium bicarbonate, and optionally monoethanolamine. It has surprisingly been found that hair color bases comprising a buffer system according to the disclosure provide compositions and methods that can lift the color of hair and/or deposit color onto hair in an unexpectedly efficient manner, resulting in a reduced processing time. In various embodiments, a plateau effect of the change in hair color is seen after about 5 to about 20 minutes, demonstrating the end of the processing time providing a controlled alteration in the color of the hair.

The buffer system comprises ammonium hydroxide in an amount ranging from about 0.1% to about 10%, such as, for example, about 0.5% to about 8%, about 1% to about 7%, about 2% to about 6%, or about 2.5% to about 5% by weight, relative to the weight of the hair color base. In various embodiments, the buffer system comprises ammonium hydroxide in an amount ranging from about 1% to about 6%, about 1% to about 5%, about 1% to about 4%, about 2% to about 6%, about 2% to about 5%, about 2% to about 4%, about 3% to about 6%, about 3% to about 5%, or about 3% to about 4%, by weight, relative to the weight of the hair color base. In further embodiments, the buffer system comprises ammonium hydroxide in an amount ranging from about 2.5% to about 4.75%, about 3% to about 4.5%, about 3.25% to about 4.25%, or about 3.5% to about 4% by weight, relative to the weight of the hair color base. In some embodiments, the buffer system comprises ammonium hydroxide in an amount of about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, about 5%, about 5.1%, about 5.2%, about 5.3%, about 5.4%, or about 5.5% by weight, relative to the weight of the hair color base, including all ranges and subranges using any of the foregoing as upper or lower limits.

The buffer system comprises ammonium bicarbonate in an amount ranging from about 0.01% to about 5%, such as, for example, about 0.1% to about 3%, about 0.25% to about 2.5%, about 0.5% to about 2%, about 0.75% to about 1.5%, or about 0.8% to about 1.2% by weight, relative to the weight of the hair color base. In various embodiments, the buffer system comprises ammonium bicarbonate in an amount ranging from about 0.1% to about 2.5%, about 0.5% to about 2%, about 0.75% to about 1.75%, or about 0.85% to about 1.5% by weight, relative to the weight of the hair color base. In further embodiments, the buffer system comprises ammonium bicarbonate in an amount ranging from about 0.25% to about 3%, about 0.5% to about 2%, or about 0.75% to about 1.25% by weight, relative to the weight of the hair color base. In some embodiments, the buffer system comprises ammonium bicarbonate in an amount of about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, or about 2.5% by weight, relative to the weight of the hair color base, including all ranges and subranges using any of the foregoing as upper or lower limits.

If present, the buffer system comprises monoethanolamine in an amount ranging from about 0.01% to about 5%, such as about 0.1% to about 5%, or about 0.5% to about 5% by weight, relative to the weight of the hair color base. In various embodiments, the buffer system comprises monoethanolamine in an amount ranging from about 0.1% to about 4%, about 0.5% to about 3.5%, about 0.75% to about 3%, or about 1% to about 2.5% by weight, relative to the weight of the hair color base. In further embodiments, the buffer system comprises monoethanolamine in an amount ranging from about 0.1% to about 3%, about 0.25% to about 2.5%, about 0.3% to about 2%, about 0.4% to about 1.75%, or about 0.5% to about 1.5% by weight, relative to the weight of the hair color base. In some embodiments, the buffer system comprises monoethanolamine (i.e. monoethanolamine is present in an amount greater than 0%) in an amount less than about 3%, such as less than about 2.5% or less than about 2% by weight, relative to the weight of the hair color base. In some embodiments, the buffer system comprises monoethanolamine in an amount of about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, or about 5% by weight, relative to the weight of the hair color base, including all ranges and subranges using any of the foregoing as upper or lower limits. In some embodiments, the buffer system comprises from about 0.1% to about 3%, preferably about 0.5% to about 2.5%, more about preferably 0.75% to about 2%, most preferably about 1% to about 1.5% monoethanolamine by weight, relative to the weight of the hair color base.

In various embodiments, it may be particularly advantageous to choose an amount of ammonium hydroxide in the buffer system in the hair color base that is greater than the amount of ammonium bicarbonate. For example, in various embodiments the buffer system in the hair color base comprises at least about 2 times more ammonium hydroxide than ammonium bicarbonate, such as at least about 2.5 times, at least about 3 times, at least about 3.5 times, or at least about 4 times more ammonium hydroxide than ammonium bicarbonate. Thus, in certain embodiments, the weight ratio of ammonium hydroxide in the buffer system to ammonium bicarbonate in the buffer system is greater than 1, for example greater than about 1.25, greater than about 1.5, greater than about 1.75, greater than about 2, greater than about 2.25, greater than about 2.5, greater than about 2.75, greater than about 3, greater than about 3.25, greater than about 3.5, greater than about 3.75, or greater than about 4, any of which may optionally range up to about 10, up to about 8, up to about 6, or up to about 5. For example, the weight ratio of ammonium hydroxide in the buffer system to ammonium bicarbonate in the buffer system may range from about 1 to about 10, from about 1 to about 8, from about 1 to about 6, from about 1 to about 5, from about 2 to about 10, from about 2 to about 8, from about 2 to about 6, from about 2 to about 5, from about 3 to about 10, from about 3 to about 8, from about 3 to about 6, or from about 3 to about 5.

Likewise, it has been surprisingly discovered that including ammonium hydroxide and ammonium bicarbonate in the cream or emulsion hair color base in amounts providing particular mole ratios of ammonium hydroxide to ammonium bicarbonate unexpectedly permits hair color altering compositions prepared using the cream or emulsion hair color base to maintain the ability to effectively impart color to the hair in less than about 25 minutes, preferably less than about 20 minutes, more preferably less than about 15 minutes, and most preferably about 10 minutes or about 10 to about 15 minutes, and protecting the hair from damage caused by over processing. Thus, in certain embodiments, the cream or emulsion hair color base composition comprises a buffer system where the molar ratio of ammonium hydroxide to ammonium bicarbonate is at least about 1.2, preferably at least about 1.5, such as, for example, greater than about 1.5, greater than about 1.55, greater than about 1.6, greater than about 1.65, greater than about 1.7, greater than about 1.75, greater than about 1.8, greater than about 1.85, greater than about 1.9, greater than about 1.95, greater than about 2.0, greater than about 2.05, greater than about 2.1, greater than about 2.15, greater than about 2.2, greater than about 2.25, greater than about 2.3, greater than about 2.35, greater than about 2.4, greater than about 2.45, greater than about 2.5, greater than about 2.55, greater than about 2.6, greater than about 2.65, greater than about 2.7, greater than about 2.75, greater than about 2.8, greater than about 2.85, greater than about 2.9, greater than about 2.95, greater than about 3.0, greater than about 3.05, greater than about 3.1, greater than about 3.15, greater than about 3.2, greater than about 3.25, greater than about 3.3, greater than about 3.35, greater than about 3.4, greater than about 3.45, greater than about 3.5, greater than about 3.55, greater than about 3.6, greater than about 3.65, greater than about 3.7, greater than about 3.75, greater than about 3.8, greater than about 3.85, greater than about 3.9, greater than about 3.95, or greater than about 4, any of which may optionally range up to about 10, up to about 8, up to about 6, or up to about 5.

For example, the buffer system in the hair color base may have a molar ratio of ammonium hydroxide to ammonium bicarbonate of about 1.5, about 1.55, about 1.6, about 1.65, about 1.7, about 1.75, about 1.8, about 1.85, about 1.9, about 1.95, about 2.0, about 2.05, about 2.1, about 2.15, about 2.2, about 2.25, about 2.3, about 2.35, about 2.4, about 2.45, about 2.5, about 2.55, about 2.6, about 2.65, about 2.7, about 2.75, about 2.8, about 2.85, about 2.9, about 2.95, about 3.0, about 3.05, about 3.1, about 3.15, about 3.2, about 3.25, about 3.3, about 3.35, about 3.4, about 3.45, about 3.5, about 3.55, about 3.6, about 3.65, about 3.7, about 3.75, about 3.8, about 3.85, about 3.9, about 3.95, or about 4, including all ranges and subranges thereof using any of the foregoing as upper or lower limits.

The molar ratio of ammonium hydroxide to ammonium bicarbonate may range from about 1.5 to about 2, from about 1.5 to about 2.5, from about 1.5 to about 3, from about 1.5 to about 3.5, or from about 1.5 to about 4, such as from about 1.55 to about 2, about 1.6 to about 2, about 1.65 to about 2, about 1.7 to about 2, about 1.75 to about 2, about 1.8 to about 2, about 1.85 to about 2, about 1.9 to about 2, about 1.95 to about 2, about 1.55 to about 3, about 1.6 to about 3, about 1.65 to about 3, about 1.7 to about 3, about 1.75 to about 3 about 1.8 to about 3, about 1.85 to about 3, about 1.9 to about 3, about 1.95 to about 3, about 2.0 to about 3, about 2.05 to about 3, about 2.1 to about 3, about 2.15 to about 3, about 2.2 to about 3, about 2.25 to about 3, about 2.3 to about 3, about 2.35 to about 3, about 2.4 to about 3, about 2.45 to about 3, about 2.5 to about 3, about 2.55 to about 3, about 2.6 to about 3, about 2.65 to about 3, about 2.7 to about 3, about 2.75 to about 3, about 2.8 to about 3, about 2.85 to about 3, about 2.9 to about 3, about 2.95 to about 3, about 1.55 to about 4, about 1.6 to about 4, about 1.65 to about 4, about 1.7 to about 4, about 1.75 to about 4 about 1.8 to about 4, about 1.85 to about 4, about 1.9 to about 4, about 1.95 to about 4, about 2.0 to about 4, about 2.05 to about 4, about 2.1 to about 4, about 2.15 to about 4, about 2.2 to about 4, about 2.25 to about 4, about 2.3 to about 4, about 2.35 to about 4, about 2.4 to about 4, about 2.45 to about 4, about 2.5 to about 4, about 2.55 to about 4, about 2.6 to about 4, about 2.65 to about 4, about 2.7 to about 4, about 2.75 to about 4, about 2.8 to about 4, about 2.85 to about 4, about 2.9 to about 4, about 2.95 to about 4, about 3.0 to about 4, about 3.05 to about 4, about 3.1 to about 4, about 3.15 to about 4, about 3.2 to about 4, about 3.25 to about 4, about 3.3 to about 4, about 3.35 to about 4, about 3.4 to about 4, about 3.45 to about 4, about 3.5 to about 4, about 3.55 to about 4, about 3.6 to about 4, about 3.65 to about 4, about 3.7 to about 4, about 3.75 to about 4, about 3.8 to about 4, about 3.85 to about 4, about 3.9 to about 4, or about 3.95 to about 4.

The molar ratio of ammonium hydroxide to ammonium bicarbonate may also range from about 1.55 to about 3.65, such as from about 1.6 to about 3.6, about 1.65 to about 3.55, such as from about 1.7 to about 3.5, from about 1.75 to about 3.45, such as about 1.8 to about 3.4, about 1.85 to about 3.35, such as about 1.9 to about 3.3, about 1.95 to about 3.25, such as about 2.0 to about 3.2, about 2.05 to about 3.15, such as about 2.1 to about 3.1, about 2.15 to about 3.05, such as from about 2.2 to about 3.0, about 2.25 to about 2.95, such as about 2.3 to about 2.9, about 2.35 to about 2.85, about such as 2.4 to about 2.8, about 2.45 to about 2.75, such as about 2.5 to about 2.7, about 2.55 to about 2.65, such as about 2.6, from about 1.55 to about 2.95, such as from about 1.6 to about 2.9, from about 1.55 to about 2.95, such as from about 1.6 to about 2.9, about 1.65 to about 2.85, such as from about 1.7 to about 2.8, about 1.75 to about 2.75, such as from about 1.8 to about 2.7, about 1.85 to about 2.65, such as from about 1.9 to about 2.6, about 1.95 to about 2.55, such as form about 2.0 to about 2.5, about 2.15 to about 2.45, such as from about 2.2 to about 2.4, about 2.25 to about 2.35, such as about 2.3, about 1.55 to about 1.95, such as from about 1.6 to about 1.9, about 1.65 to about 1.85, or about 1.7 to about 1.8, or about 1.75.

In some exemplary embodiments, the molar ratio of ammonium hydroxide to ammonium bicarbonate ranges from about 1.2 to about 3.75, from about 1.2 to about 3.65, from about 1.5 to about 3.75, from about 1.5 to about 3.65, or from about 1.75 to about 3.65. In other exemplary embodiments, the molar ratio of ammonium hydroxide to ammonium bicarbonate ranges from about 1.2 to about 2.5, from about 1.2 to about 2.25, from about 1.2 to about 2, from about 1.2 to about 1.8, from about 1.5 to about 2.5, from about 1.5 to about 2.25, from about 1.5 to about 2, from about 1.5 to about 1.8, from about 1.65 to about 2.5, from about 1.65 to about 2.25, from about 1.65 to about 2, or from about 1.65 to about 1.8.

In various exemplary and non-limiting embodiments, the buffer system in the hair color base comprises, based on the total weight of the hair color base, from about 1% to about 6%, preferably from about 1.5% to about 5%, about 2% to about 4.75%, about 2.5% to about 4.5%, or about 2.5% to about 4% of ammonium hydroxide; from about 0.1% to about 2.5%, preferably from about 0.2% to about 2.25%, about 0.3% to about 2%, about 0.4% to about 1.75%, or about 0.5% to about 1.5% of ammonium bicarbonate; and optionally, from about 0.1% to about 5%, such as from about 0.5% to about 2.5% of monoethanolamine. In a further exemplary and non-limiting embodiment, the buffer system in the hair color base comprises, based on the total weight of the hair color base, from about 1% to about 6%, preferably from about 1.5% to about 5%, about 2% to about 4.75%, about 2.5% to about 4.5%, or about 2.5% to about 4% of ammonium hydroxide; from about 0.1% to about 2.5%, preferably from about 0.2% to about 2.25%, about 0.3% to about 2%, about 0.4% to about 1.75%, or about 0.5% to about 1.5% of ammonium bicarbonate; and optionally, from about 0.1% to about 5%, such as from about 0.5% to about 2.5% of monoethanolamine, wherein the hair color base has a molar ratio of ammonium hydroxide to ammonium bicarbonate greater than about 1.5, greater than about 1.55, greater than about 1.6, greater than about 1.65, greater than about 1.7, or greater than about 1.75.

For example, the buffer system in the hair color base may include about 3% to about 5% ammonium hydroxide, about 0.5% to about 1.5% ammonium bicarbonate, and optionally from about 0.5% to about 2.5% monoethanolamine, all weights based on the total weight of the hair color base. In certain preferred embodiments, the buffer system in the hair color base has a molar ratio of ammonium hydroxide to ammonium bicarbonate greater than about 1.5.

In a further example, the buffer system in the hair color base may include about 3.25% to about 4.75% ammonium hydroxide, about 0.75% to about 1.25% ammonium bicarbonate, and optionally from about 0.5% to about 2.5% monoethanolamine, all weights based on the total weight of the hair color base. Preferably, in certain embodiments, the buffer system in the hair color base has a molar ratio of ammonium hydroxide to ammonium bicarbonate greater than about 1.5.

In yet a further example, the buffer system in the hair color base may include about 3.25% to about 4.5% ammonium hydroxide, about 0.8% to about 1.2% ammonium bicarbonate, and optionally from about 1% to about 2% monoethanolamine, all weights based on the total weight of the hair color base. Preferably, in certain embodiments, the buffer system in the hair color base has a molar ratio of ammonium hydroxide to ammonium bicarbonate greater than about 1.5.

In a still further example, the buffer system in the hair color base may include about 3.5% to about 4% ammonium hydroxide, about 0.75% to about 1.25% ammonium bicarbonate, and optionally from about 0.75% to about 2% monoethanolamine, all weights based on the total weight of the hair color base. Preferably, in certain embodiments, the buffer system in the hair color base has a molar ratio of ammonium hydroxide to ammonium bicarbonate greater than about 1.5.

In some exemplary and non-limiting embodiments, the buffer system in the hair color base does not include ammonium hydroxide in an amount greater than about 5%, for example the amount of ammonium hydroxide is not greater than about 4.75%, not greater than about 4.5%, not greater than about 4.25%, or not greater than about 4% by weight, relative to the total weight of the hair color base.

In still further exemplary and non-limiting embodiments, the buffer system of the hair color base does not include monoethanolamine in an amount greater than about 3% or greater than about 2.5%, for example the amount of monoethanolamine is, in certain embodiments, not greater than about 2.25%, not greater than about 2%, not greater than about 1.75%, or not greater than about 1.5% by weight, relative to the total weight of the hair color base.

Additional Components

The hair color base may optionally comprise additional components, including, but not limited to, colorant compounds, solvents, fatty substances, rheology modifiers or thickening agents, cationic polymers, and/or auxiliary components, but the skilled person will choose such components with care to maintain a pH of the hair color base and/or the degree of lift imparted within an acceptable variation.

Colorant

The hair color base according to the disclosure may optionally comprise at least one colorant, or as an alternate embodiment, one or more colorants may be present in a separate composition that is mixed with the hair color base before use. In one embodiment, the hair color base comprises at least one colorant compound chosen from oxidation dyes and/or direct dyes.

In various embodiments, the at least one colorant may be chosen from oxidation dyes, direct dyes, pigments, or mixtures thereof.

In certain embodiments, the hair color base may contain resorcinol and/or resorcinol derivatives, or may exclude resorcinol and/or resorcinol derivatives.

The oxidation dyes are generally chosen from one or more oxidation bases optionally combined with one or more couplers. By way of example, the oxidation bases are chosen from para-phenylenediamines, bis(phenyl)alkylenediamines, para-aminophenols, ortho-aminophenols, meta-aminophenols, and heterocyclic bases, and the addition salts thereof.

Among the para-phenylenediamines that may be mentioned, for example, are para-phenylenediamine, para-toluenediamine (toluene-2,5-diamine), 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N, N-diethyl-para-phenylenediamine, N, N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl) amino-2-methylaniline, 4-N,N-bis(β-hydroxyethyl)amino-2-chloroaniline, 2-β-hydroxyethyl-para-phenylenediamine, 2-methoxymethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β, γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, hydroxypropyl bis(n-hydroxyethyl-p-phenylenediamine, and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, may be chosen.

Among the bis(phenyl)alkylenediamines that may be mentioned, for example, are N,N'-bis(β-hydroxyethyl)-N, N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof. Among the meta-aminophenols, 3-aminophenol and salts thereof, may be mentioned.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the present disclosure are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino] ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-α-hydroxyethoxy-3-amino-pyrazolo[1,5-a]pyridine; 2-(4-dimethylpyperazinium-1-yl)-3-amino-pyrazolo[1,5-a]pyridine; hydroxyethoxy aminopryazolopyridine, and the addition salts thereof.

Further exemplary oxidation bases that are useful in the present disclosure are selected from 3-aminopyrazolo-[1,5-a]-pyridines and optionally substituted on carbon atom 2 by: (i) one (di)($C_1$-$C_6$)(alkyl)amino group wherein said alkyl group can be substituted by at least one hydroxy, amino, imidazolium group; (ii) one heterocycloalkyl group containing from 5 to 7 members chain, and from 1 to 3 heteroatoms, potentially cationic, potentially substituted by one or more ($C_1$-$C_6$)alkyl, such as di($C_1$-$C_4$) alkylpipérazinium; or (iii) one ($C_1$-$C_6$)alkoxy potentially substituted by one or more hydroxy groups such as α-hydroxyalkoxy, and the addition salts thereof.

Among the pyrimidine derivatives that may be mentioned are the compounds described, for example, in the patents DE 2359399; JP 88-169571; JP 05-63124; EP 0770375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are the compounds described in the patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-β-hydroxyethyl)pyrazole, 3,4-diaminopyrazole, 4,5-diamino-1-(4'-chlorobenzyl) pyrazole, 4,5-diamino-1,3-dimethylpyrazole, 4,5-diamino-3-methyl-1-phenylpyrazole, 4,5-diamino-1- methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropyl-pyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-β-hydroxyethyl) amino-1-methylpyrazole, and the addition salts thereof. 4,5-Diamino-1-β-methoxyethyl)pyrazole may also be used. According to some embodiments, 2,3-diaminodihydropyrazolo pyrazolone dimethosulfonate may also be used. Optionally, a 4,5-diaminopyrazole may be used, for example 4,5-diamino-1-β-hydroxyethyl)pyrazole and/or a salt thereof.

Pyrazole derivatives that may also be mentioned include diamino-N,N-dihydropyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, and 2,3-diamino-6-hydroxy-6,7-dihydro-1H,5H-pyrazolo[1,2-a]pyrazol-1-one. For example, 2,3-Diamino-6,7-dihydro-1H, 5H-pyrazolo[1,2-a]pyrazol-1-one and/or a salt thereof may be used.

According to some embodiments, 2,3-diaminodihydropyrazolo pyrazolone dimethosulfonate may be used. 4,5-Diamino-1-β-hydroxyethyl)pyrazole and/or 2,3-diamino-6,7-dihydro-1H, 5H-pyrazolo[1,2-a]pyrazol-1-one and/or a salt thereof may be used as heterocyclic bases.

Compositions according to the invention may optionally comprise one or more couplers advantageously chosen from those conventionally used in the dyeing or coloring of keratin fibers, e.g. hair. Among these couplers, mention may be made especially of meta-phenylenediamines, meta-aminophenols, meta-diphenols, naphthalene-based couplers and heterocyclic couplers, and also the addition salts thereof.

Mention may be made, for example, of 2-methyl-5-aminophenol, 5-N-(β-hydroxyethyl) amino-2-methylphenol, 3-aminophenol, 5-amino-6-chloro-o-cresol (3-amino-2-chloro-6-methylphenol), 1,3-dihydroxybenzene, 1,3-dihydroxy-2-methyl-benzene, 4-chloro-1,3-dihydroxybenzene, 2,4-diamino-1-(β-hydroxyethyloxy) benzene (2,4 diaminophenoxyethanol HCL), 2-amino-4-(β-hydroxyethylamino)-1-methoxy-benzene (2-methyl-5-hydroxyethylaminophenol), 1,3-diaminobenzene, 1,3-bis(2,4-diaminophenoxy) propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl) amino-3,4-methylenedioxybenzene, 2,6-bis(β-hydroxyethylamino)-toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole, 4-amino-2-hydroxytoluene, 2-methylresorcinol, 4-chlororesorcinol, and 6-methylpyrazolo[1,5-a]benzimidazole, the addition salts thereof with an acid, or mixtures thereof.

In general, the addition salts of the oxidation bases and couplers that may be used in the context of the invention are especially selected from the addition salts with an acid such as the hydrochlorides, hydrobromides, sulfates, citrates, succinates, tartrates, lactates, tosylates, benzenesulfonates, phosphates and acetates.

The total amount of oxidation base(s) may, for example, range from about 0.001% to about 10% by weight, relative to the total weight of the composition, such as from about 0.005% to about 5% by weight, relative to the total weight of the composition.

The coupler(s), if they are present, each advantageously represent from about 0.001% to about 10% by weight, relative to the total weight of the composition, such as from about 0.005% to about 5% by weight, relative to the total weight of the composition.

Compositions according to the invention may optionally comprise one or more synthetic or natural direct dyes, chosen from anionic and nonionic species, e.g. cationic or nonionic species, either as sole dyes or in addition to oxidation dye(s).

Examples of suitable direct dyes that may be mentioned include azo direct dyes; (poly)methine dyes such as cyanins, hemicyanins and styryls; carbonyl dyes; azine dyes; nitro (hetero)aryl dyes; tri(hetero)arylmethane dyes; porphyrin dyes; phthalocyanin dyes, and natural direct dyes, alone or as mixtures.

In various embodiments, direct dyes are cationic direct dyes. Mention may be made of the hydrazono cationic dyes of formulas (Va) and (V'a), the azo cationic dyes (VIa) and (VI'a) and the diazo cationic dyes (VIIa) below:

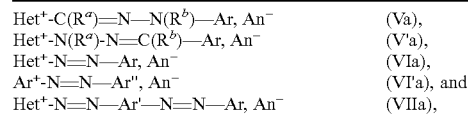

| | |
|---|---|
| Het⁺-C(R$^a$)=N—N(R$^b$)—Ar, An⁻ | (Va), |
| Het⁺-N(R$^a$)-N=C(R$^b$)—Ar, An⁻ | (V'a), |
| Het⁺-N=N—Ar, An⁻ | (VIa), |
| Ar⁺-N=N—Ar'', An⁻ | (VI'a), and |
| Het⁺-N=N—Ar'—N=N—Ar, An⁻ | (VIIa), | in which formulas (Va), (V'a), (VIa), (VI'a), and (VIIa): Het⁺ represents a cationic heteroaryl radical, optionally bearing an endocyclic cationic charge, such as imidazolium, indolium or pyridinium, optionally substituted preferentially with one or more ($C_1$-$C_8$) alkyl groups such as methyl;

Ar⁺ representing an aryl radical, such as phenyl or naphthyl, bearing an exocyclic cationic charge, preferentially ammonium, particularly tri($C_1$-$C_8$)alkylammonium such as trimethylammonium;

Ar represents an aryl group, especially phenyl, which is optionally substituted, preferentially with one or more electron-donating groups such as i) optionally substituted ($C_1$-$C_8$)alkyl, ii) optionally substituted ($C_1$-$C_8$)alkoxy, iii) (di)($C_1$-$C_8$)(alkyl)amino optionally substituted on the alkyl group(s) with a hydroxyl group, iv) aryl($C_1$-$C_8$)alkylamino, v) optionally substituted N-($C_1$-$C_8$)alkyl-N-aryl($C_1$-$C_8$)alkylamino or alternatively Ar represents a julolidine group;

Ar' is an optionally substituted divalent (hetero)arylene group such as phenylene, particularly para-phenylene, or naphthalene, which are optionally substituted, preferentially with one or more groups $(C_1-C_8)$alkyl, hydroxyl or $(C_1-C_8)$ alkoxy;

$Ar^+$ is an optionally substituted (hetero)aryl group such as phenyl or pyrazolyl, which are optionally substituted, preferentially with one or more groups $(C_1-C_8)$alkyl, hydroxyl, $(di)(C_1-C_8)(alkyl)$amino, $(C_1-C_8)$alkoxy or phenyl;

$R^a$ and $R^b$, which may be identical or different, represent a hydrogen atom or a group $(C_1-C_8)$alkyl, which is optionally substituted, preferentially with a hydroxyl group; or alternatively the substituent $R^a$ with a substituent of $Het^+$ and/or $R^b$ with a substituent of Ar and/or $R^a$ with $R^b$ form, together with the atoms that bear them, a (hetero)cycloalkyl; particularly, $R^a$ and $R^b$ represent a hydrogen atom or a group $(C_1-C_4)$alkyl, which is optionally substituted with a hydroxyl group; and $An^-$ represents an anionic counter-ion such as mesylate or halide.

In particular, mention may be made of the azo and hydrazono cationic dyes bearing an endocyclic cationic charge of formulae (Va), (V'a), and (VIa) as defined previously. More particularly, those dyes of formulae (Va), (V'a), and (VIa) derived from the dyes described in patent applications WO 95/15144, WO 95/01772 and EP-714954 may be chosen.

In various embodiments, the cationic part is derived from the following derivatives:

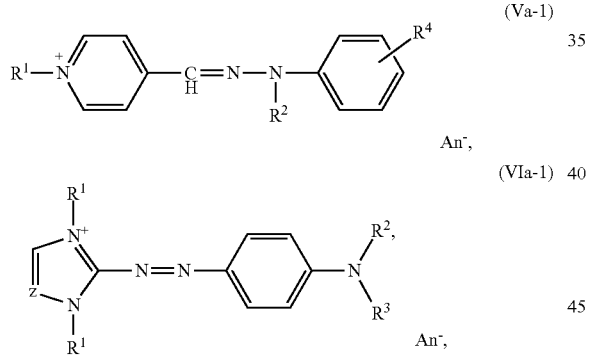

wherein:

$R^1$ representing a $(C_1-C_4)$ alkyl group such as methyl;

$R^2$ and $R^3$, which are identical or different, represent a hydrogen atom or a $(C_1-C_4)$alkyl group, such as methyl; and $R^4$ represents a hydrogen atom or an electron-donating group such as optionally substituted $(C_1-C_8)$alkyl, optionally substituted $(C_1-C_8)$alkoxy, or $(di)(C_1-C8)(alkyl)$amino optionally substituted on the alkyl group(s) with a hydroxyl group; particularly, $R^4$ is a hydrogen atom, Z represents a CH group or a nitrogen atom, preferentially CH; and $An^-$ represents an anionic counter-ion such as mesylate or halide.

In various embodiments, the dye chosen from formulae (Va-1) or (VIa-1) is chosen from Basic Red 51, Basic Yellow 87, Basic Orange 31, derivatives thereof, or mixtures thereof:

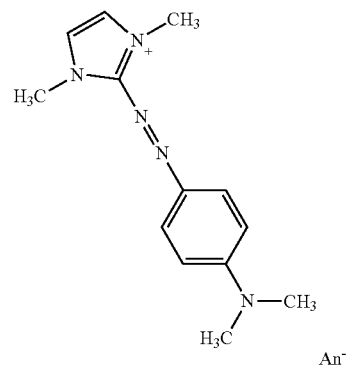

Basic Red 51

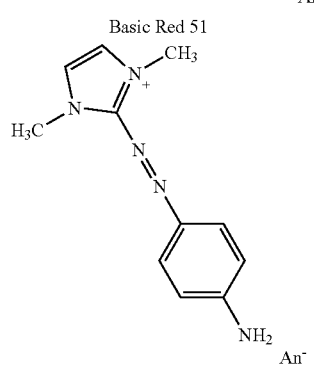

Basic Orange 31

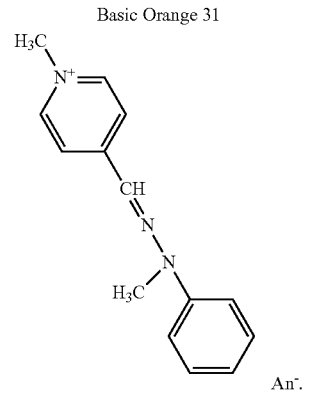

Basic Yellow 87

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin, apigenidin and orceins. Extracts or decoctions containing these natural dyes such as henna-based poultices or extracts may also be used.

When present, the total amount of direct dye(s) may range from 0.001% to 10%, such as from 0.005% to 5% by weight, relative to the total weight of the composition.

Exemplary and non-limiting pigments that may be used include organic and/or mineral pigments known in the art, such as those described in Kirk-Othmer's chemical technology encyclopedia and in Ullmann's industrial chemistry encyclopedia, including but not limited to mineral pigments, organic pigments, lakes, pigments with special effects such as nacres or glitter flakes, or mixtures thereof. These pigments may be in the form of a powder or pigmentary paste, and may be coated or uncoated.

Among the mineral pigments that are useful, non-limiting mention may be made of iron oxides, chromium oxides, manganese violet, ultramarine blue, chromium hydrate, ferric blue, and titanium oxides.

Non-limiting examples of organic pigments include nitroso, nitro, azo, xanthene, quinoline, anthraquinone, phthalocyanin, metal-complex, isoindolinone, isoindoline, quinacridone, perinone, perylene, diketopyrrolopyrrole, thioindigo, dioxazine, triphenylmethane and quinophthalone compounds. For example, carmine, carbon black, aniline black, azo yellow, quinacridone, phthalocyanin blue, sorghum red, the blue pigments codified in the Color Index under the references CI 42090, 69800, 69825, 73000, 74100, and 74160, the yellow pigments codified in the Color Index under the references CI 11680, 11710, 15985, 19140, 20040, 21100, 21108, 47000, and 47005, the green pigments codified in the Color Index under the references CI 61565, 61570, and 74260, the orange pigments codified in the Color Index under the references CI 11725, 15510, 45370, and 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915, and 75470, and the pigments obtained by oxidative polymerization of indole or phenolic derivatives as described in patent FR 2679771 may be chosen.

The pigments may also be chosen from lakes, which are understood to refer to dyes adsorbed onto insoluble particles, the assembly thus obtained remaining insoluble during use. The inorganic particles or substrates onto which the dyes are adsorbed include, for example, alumina, silica, calcium sodium borosilicate or calcium aluminum borosilicate, and aluminum. Among the dyes that can be adsorbed thereon, non-limiting mention may be made of cochineal carmine and the following dyes: D&C Red 21 (CI 45 380), D&C Orange 5 (CI 45 370), D&C Red 27 (CI 45 410), D&C Orange 10 (CI 45 425), D&C Red 3 (CI 45 430), D&C Red 4 (CI 15 510), D&C Red 33 (CI 17 200), D&C Yellow 5 (CI 19 140), D&C Yellow 6 (CI 15 985), D&C Green (CI 61 570), D&C Yellow 10 (CI 77 002), D&C Green 3 (CI 42 053), D&C Blue 1 (CI 42 090).

When present, the pigment(s) may, for example, be present in an amount ranging from 0.001% to 10% by weight, such as from 0.005% to 5% by weight of the total weight of the composition.

Solvents

The hair color base according to the disclosure may comprise a cosmetically acceptable solvent, for example as a dye support when a hair dye composition is contemplated. The cosmetically acceptable solvent can comprise water or a mixture of water and at least one cosmetically acceptable organic solvent.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol.

Other suitable examples of organic solvents are ethylene glycol, propylene glycol, butylene glycol, hexylene glycol, propane diol, and glycerin. The organic solvents for use according to the present disclosure can be volatile or non-volatile compounds.

In some embodiments, the total amount of organic solvents may range from about 0.1% to about 25% by weight, such as from about 1% to about 15% by weight, from about 2% to about 8% by weight, from about 3% to about 7% by weight, or such as about 4% to 6% by weight, based on the total weight of the hair color base. In other embodiments, the amount of an individual organic solvent may range from about 0.1% to about 25% by weight, such as from about 1% to about 15% by weight, from about 2% to about 8% by weight, from about 3% to about 7% by weight, or such as about 4% to 6% by weight, based on the total weight of the hair color base For example, the hair color base may include 0.6% of a carbomer (4% solution).

In various exemplary embodiments, the cosmetically acceptable solvent may be employed according to the present disclosure in an amount ranging from about 1% to about 60% by weight, or such as from about 5% to about 30% by weight, such as from about 5% to about 25% by weight, or such as from about 5% to about 20% by weight, based on the total weight of the hair color base.

Fatty Substances

The hair color base according to the disclosure may comprise at least one fatty substance. Alternatively, one or more fatty substances may be present in a separate composition that is mixed with the hair color base before use.

"Fatty substance" means an organic compound insoluble in water at normal temperature (25° C.) and at atmospheric pressure (750 mmHg) (solubility below 5% and such as below 1% and further such as below 0.1%). Fatty substances have in their structure a chain of at least two siloxane groups or at least one hydrocarbon chain having at least 6 carbon atoms. Moreover, fatty substances are generally soluble in organic solvents in the same conditions of temperature and pressure, for example in chloroform, ethanol, benzene, or decamethylcyclopentasiloxane.

Fatty substances are, for example, chosen from alkanes, fatty alcohols, esters of fatty acid, esters of fatty alcohol, oils such as mineral, vegetable, animal and synthetic non-silicone oils, non-silicone waxes, silicones, or mixtures thereof.

When present, the fatty compounds and/or oils will typically be present in the hair color base in an amount ranging from about 0.05% to about 30% by weight, such as from about 0.1% to 20% by weight, from about 1% to about 12% by weight, or from about 5% to about 9% by weight, based on the total weight of the hair color base.

In some embodiments, the alcohols and esters have at least one linear or branched, saturated or unsaturated hydrocarbon group, comprising 6 to 30 carbon atoms, optionally substituted, for example, with at least one hydroxyl group (for example 1 to 4). If they are unsaturated, these compounds can have one to three, conjugated or unconjugated, carbon-carbon double bonds.

With regard to the alkanes, in some embodiments, these have from 6 to 16 carbon atoms and are linear or branched, optionally cyclic. As examples, alkanes can be chosen from hexane and dodecane, isoparaffins such as isohexadecane, isododecane, and isodecane.

Non-limiting examples of non-silicone oils according to the disclosure, include: hydrocarbon oils of animal origin, such as perhydrosqualene; hydrocarbon oils of vegetable origin, such as liquid triglycerides of fatty acids having from 6 to 30 carbon atoms such as oleic acid, triglycerides of heptanoic or octanoic acids, or for example sunflower oil, maize oil, soya oil, cucurbit oil, grapeseed oil, sesame oil, hazelnut oil, apricot oil, macadamia oil, arara oil, sunflower oil, castor oil, avocado oil, triglycerides of caprylic/capric acids such as those sold by the company Stearineries Dubois or those sold under the names MIGLYOL® 810, 812 and 818 by the company Dynamit Nobel, jojoba oil, shea butter oil; hydrocarbons with more than 16 carbon atoms, linear or branched, of mineral or synthetic origin, such as paraffin oils, petroleum jelly, liquid paraffin, polydecenes, hydrogenated polyisobutene such as Parleam®, fluorinated, partially hydrocarbon oils; as fluorinated oils, non-limiting examples include perfluoromethylcyclopentane and perfluoro-1,3-dimethylcyclohexane, sold under the names "FLUTEC® PC1" and "FLUTEC® PC3" by the company F2 Chemicals Ltd.; perfluoro-1,2-dimethylcyclobutane; perfluoroalkanes such as dodecafluoropentane and tetradecafluorohexane, sold under the names "PF 5050®" and "PF 5060®" by the 3M Company, or bromoperfluorooctyl sold under the name "FORALKYL®" by the company Atochem; nonafluoromethoxybutane and nonafluoroethoxyisobutane; derivatives of perfluoromorpholine, such as 4-trifluoromethyl perfluoromorpholine sold under the name "PF 5052®" by the 3M Company.

The fatty alcohols usable as fatty substances according to the disclosure include, but are not limited to, non-alkoxylated, saturated or unsaturated, linear or branched, and have from 6 to 30 carbon atoms and more particularly from 8 to 30 carbon atoms. For example, cetyl alcohol, stearyl alcohol and their mixture (cetearyl alcohol), octyldodecanol, 2-butyloctanol, 2-hexyldecanol, 2-undecylpentadecanol, oleic alcohol or linoleic alcohol may be chosen.

The exemplary non-silicone wax or waxes that can be used in the composition of the disclosure are chosen from paraffin wax, carnauba wax, candelilla wax, and Alfa wax, paraffin wax, ozokerite, vegetable waxes such as olive wax, rice wax, hydrogenated jojoba wax or absolute waxes of flowers such as the essential wax of blackcurrant flower sold by the company BERTIN (France), animal waxes such as beeswaxes, or modified beeswaxes (cerabellina); other waxes or waxy raw materials usable according to the disclosure include but are not limited to marine waxes such as that sold by the company SOPHIM under reference M82, waxes of polyethylene or of polyolefins in general.

The exemplary fatty acid esters are the esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total number of carbons of the esters being, for example, greater than or equal to 10.

Among the monoesters, non-limiting examples include dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso) stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, ethyl-2-hexyl palmitate, 2-octyldecyl palmitate, alkyl myristates such as isopropyl, butyl, cetyl, 2-octyldodecyl, mirystyl, stearyl myristate, hexyl stearate, butyl stearate, isobutyl stearate; dioctyl malate, hexyl laurate, and 2-hexyldecyl laurate.

Further non-limiting examples of esters include $C_4$-$C_{22}$ di- or tricarboxylic acids and $C_1$-$C_{22}$ alcohols and the esters of mono-, di-, or tricarboxylic acids and of $C_2$-$C_{26}$ di-, tri-, tetra- or pentahydroxy alcohols.

Even further non-limiting examples of esters include: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate, tridecyl erucate; triisopropyl citrate; triisotearyl citrate; glyceryl trilactate; glyceryl trioctanoate; trioctyldodecyl citrate; trioleyl citrate, propylene glycol dioctanoate; neopentyl glycol diheptanoate; diethylene glycol diisanonate; and polyethylene glycol distearates.

Among the esters mentioned above, particularly useful exemplary esters for various embodiments include ethyl, isopropyl, myristyl, cetyl, stearyl palmitates, ethyl-2-hexyl palmitate, 2-octyldecyl palmitate, alkyl myristates such as isopropyl, butyl, cetyl, 2-octyldodecyl myristate, hexyl stearate, butyl stearate, isobutyl stearate; dioctyl malate, hexyl laurate, 2-hexyldecyl laurate, isononyl isononanoate, cetyl octanoate, or mixtures thereof.

The composition can also comprise, as fatty ester, esters and di-esters of sugars of $C_6$-$C_{30}$, such as $C_{12}$-$C_{22}$, fatty acids. "Sugar" as used in the disclosure means oxygen-containing hydrocarbon compounds that possess several alcohol functions, with or without aldehyde or ketone functions, and having at least 4 carbon atoms. These sugars can be monosaccharides, oligosaccharides, or polysaccharides.

As suitable sugars, non-limiting examples include sucrose, glucose, galactose, ribose, fucose, maltose, fructose, mannose, arabinose, xylose, lactose, and their derivatives, for example alkylated, such as methylated derivatives, e.g. methylglucose.

The esters of sugars and of fatty acids can, for example, be chosen from the esters or mixtures of esters of sugars described previously and of linear or branched, saturated or unsaturated $C_6$-$C_{30}$, such as $C_{12}$-$C_{22}$, fatty acids. If they are unsaturated, these compounds can have one to three, conjugated or unconjugated, carbon-carbon double bonds.

The esters according to at least one embodiment can also be chosen from mono-, di-, tri-, and tetra-esters, polyesters or mixtures thereof. These esters can be for example oleate, laurate, palmitate, myristate, behenate, cocoate, stearate, linoleate, linolenate, caprate, arachidonates, or mixtures thereof such as the oleo-palmitate, oleo-stearate, palmito-stearate mixed esters.

For example, the mono- and di-esters can be used, and such as the mono- or di-oleate, stearate, behenate, oleopalmitate, linoleate, linolenate, oleostearate, of sucrose, of glucose or of methylglucose. Non-limiting mention can be made of the product sold under the name GLUCATE® DO by the company Amerchol, which is a dioleate of methylglucose.

Exemplary esters or of mixtures of esters of sugar of fatty acid include: the products sold under the names Crodesta™ F160, F140, F110, F90, F70, SL40 by the company Croda, Inc., Edison, N.J., denoting respectively the palmito-stearates of sucrose formed from 73% of monoester and 27% of di- and tri-ester, from 61% of monoester and 39% of di-, tri-, and tetra-ester, from 52% of monoester and 48% of di-, tri-, and tetra-ester, from 45% of monoester and 55% of di-, tri-, and tetra-ester, from 39% of monoester and 61% of di-, tri-, and tetra-ester, and the mono-laurate of sucrose; the products sold under the name Ryoto Sugar Esters for example with the reference B370 and corresponding to the behenate of sucrose formed from 20% of monoester and 80% of di-triester-polyester; sucrose mono-di-palmito-stearate marketed by the company Evonik under the name TEGOSOFT® PSE.

The silicones usable in the composition of the present disclosure include but are not limited to volatile or non-volatile, cyclic, linear, or branched silicones, which may be optionally modified with organic groups.

The silicones usable according to the disclosure can be in the form of oils, waxes, resins, or gums. In some embodiments, a mixture C30-45 alkyldimethylsilyl polypropylsilsesquioxane, available as SW-8005 C30 resin wax available from DOW CORNING®, and paraffin and may be included in the hair color base.

In some embodiments, the silicone is chosen from the polydialkylsiloxanes, such as the polydimethylsiloxanes (PDMS), and the organo-modified polysiloxanes having at least one functional group selected from the poly(alkoxylated) groups, the amine groups and the alkoxy groups.

The organopolysiloxanes are defined in more detail in the work of Walter NOLL "Chemistry and Technology of Silicones" (1968), Academic Press. They can be volatile or non-volatile.

When they are volatile, the silicones are, for example, chosen from those with a boiling point between 60° C. and 260° C., and for further examples, chosen from: cyclic polydialkylsiloxanes having from 3 to 7, such as from 4 to 5 silicon atoms. It can be, for example, the octamethylcyclotetrasiloxane marketed under the name VOLATILE SILICONE® 7207 by UNION CARBIDE or SILBIONE® 70045 V2 by RHODIA, the decamethylcyclopentasiloxane marketed under the name VOLATILE SILICONE® 7158 by UNION CARBIDE, and SILBIONE® 70045 V5 by RHODIA, or mixtures thereof.

Non-limiting examples include the cyclocopolymers of the dimethylsiloxanes/methylalkylsiloxane type, such as SILICONE VOLATILE® FZ 3109 marketed by the company UNION CARBIDE, of formula (I):

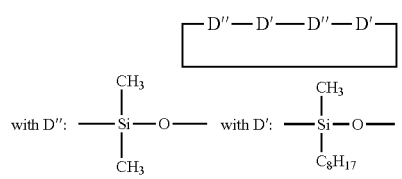

Non-limiting examples also include mixtures of cyclic polydialkylsiloxanes with organic compounds derived from silicon, such as the mixture of octamethylcyclotetrasiloxane and tetratrimethylsilylpentaerythritol (50/50) and the mixture of octamethylcyclotetrasiloxane and oxy-1,1'-(hexa-2,2,2',2',3,3'-trimethylsilyloxy) bis-neopentane.

Other suitable volatile silicones include the linear volatile polydialkylsiloxanes having 2 to 9 silicon atoms and with a viscosity less than or equal to $5 \times 10^{-6}$ m$^2$/s at 25° C. An example is decamethyltetrasiloxane, marketed under the name "Toray SH 200 Fluid" by the company DOW CORNING®. Silicones included in this class are also described in the article published in Cosmetics and Toiletries, Vol. 91, Jan. 76, p. 27-32, TODD BYERS "Volatile Silicone fluids for cosmetics."

Even further non-limiting examples include non-volatile polydialkylsiloxanes, gums, and resins of polydialkylsiloxanes, polyorganosiloxanes modified with the aforementioned organofunctional groups, or mixtures thereof.

These silicones are, for example, chosen from the polydialkylsiloxanes, such as the polydimethylsiloxanes with trimethylsilyl end groups. The viscosity of the silicones is measured at 25° C. according to standard ASTM 445 Appendix C.

Among these polydialkylsiloxanes, mention can be made of, non-exhaustively, the following commercial products: the SILBIONE® oils of series 47 and 70 047 or the MIRASIL® oils marketed by RHODIA, for example the oil 70 047 V 500 000; the oils of the MIRASIL® series marketed by the company RHODIA; the oils of the 200 series from the company DOW CORNING such as DC200; the VISCASIL® oils from GENERAL ELECTRIC and certain oils of the SF series (SF 96, SF 18) from GENERAL ELECTRIC.

Non-limiting mention can also be made of the polydimethylsiloxanes with dimethylsilanol end groups known under the name of dimethiconol (CTFA), such as the oils of the 48 series from the company RHODIA.

In this class of polydialkylsiloxanes, non-limiting mentions can be made of the products marketed under the names "ABIL WAX® 9800 and 9801" by the company Evonik, which are polydialkyl ($C_1$-$C_{20}$) siloxanes.

The silicone gums usable according to the disclosure are, for example, polydialkylsiloxanes, such as polydimethylsiloxanes with high number-average molecular weights between 200,000 and 1,000,000 used alone or mixed in a solvent. This solvent can be chosen from the volatile silicones, the polydimethylsiloxane (PDMS) oils, the polyphenylmethylsiloxane (PPMS) oils, the isoparaffins, the polyisobutylenes, methylene chloride, pentane, dodecane, tridecane, or mixtures thereof.

Products usable according to the disclosure are, for example, mixtures such as mixtures formed from a chain end hydroxylated polydimethylsiloxane, or dimethiconol (CTFA) and a cyclic polydimethylsiloxane also called cyclomethicone (CTFA), such as the product Q2 1401 marketed by the company DOW CORNING; mixtures of a polydimethylsiloxane gum and a cyclic silicone such as the product SF 1214 Silicone Fluid from the company GENERAL ELECTRIC, said product being a gum SF 30 corresponding to a dimethicone, having a number-average molecular weight of 500,000, dissolved in the oil SF 1202 Silicone Fluid corresponding to decamethylcyclopentasiloxane; mixtures of two PDMS of different viscosities, for example, of a PDMS gum and a PDMS oil, such as the product SF 1236 from the company GENERAL ELECTRIC. The product SF 1236 is a mixture of a gum SE 30 as defined above having a viscosity of 20 m$^2$/s and an oil SF 96 with a viscosity of $5 \times 10^{-6}$ m$^2$/s. This product, for example, has 15% of gum SE 30 and 85% of oil SF 96.

The organopolysiloxane resins usable according to the disclosure include but are not limited to crosslinked siloxane systems containing the units: $R_2SiO_{2/2}$, $R_3SiO_{1/2}$, $RSiO_{3/2}$, and/or $SiO_{4/2}$, in which R represents an alkyl having 1 to 16 carbon atoms. For example, R denotes a $C_1$-$C_4$ lower alkyl group such as methyl.

Among these resins, non-limiting examples include the product marketed under the name "DOW CORNING 593" or those marketed under the names "SILICONE FLUID SS 4230 and SS 4267" by the company GENERAL ELECTRIC, which are silicones of dimethyl/trimethyl siloxane structure.

Non-limiting examples also include the resins of the trimethylsiloxysilicate type, such as those marketed under the names X22-4914, X21-5034 and X21-5037 by the company SHIN-ETSU.

The organomodified silicones useful according to the disclosure include but are not limited to silicones as defined previously, having in their structure at least one organofunctional group fixed by a hydrocarbon group.

In addition to the silicones described above, the organomodified silicones can be polydiaryl siloxanes, such as polydiphenylsiloxanes, or polyalkyl-arylsiloxanes functionalized by the aforementioned organofunctional groups.

The polyalkarylsiloxanes are, for example, chosen from the polydimethyl/methylphenylsiloxanes, the polydimethyl/diphenylsiloxanes, linear and/or branched, with viscosity ranging from $1 \times 10^{-5}$ to $5 > 10^2$ m$^2$/s at 25° C.

Among these polyalkarylsiloxanes, non-limiting mentins can be made of the products marketed under the following names: the SILBIONE® oils of series 70 641 from RHODIA; the oils of the series RHODORSIL® 70 633 and 763 from RHODIA; the oil DOW CORNING 556 COSMETIC GRADE FLUID from DOW CORNING; the silicones of the PK series from BAYER such as the product PK20; the silicones of the series PN, PH from BAYER such as the products PN1000 and PH1000; certain oils of the SF series from GENERAL ELECTRIC such as SF 1023, SF 1154, SF 1250, or SF 1265.

Among the organomodified silicones, non-limiting mention can be made of the polyorganosiloxanes having: polyoxyethylene and/or polyoxypropylene groups optionally with $C_6$-$C_{24}$ alkyl groups such as the products called dimethicone copolyol marketed by the company DOW CORNING under the name DC 1248 or the oils SILWET® L 722, L 7500, L 77, L 711 from the company UNION CARBIDE and the alkyl ($C_{12}$)-methicone copolyol marketed by the company DOW CORNING under the name Q2 5200; substituted or unsubstituted amine groups such as the products marketed under the name GP 4 Silicone Fluid and GP 7100 by the company Genesee Polymers, or the products marketed under the names Q2 8220 and DOW CORNING 929 or 939 by the company DOW CORNING. The substituted amine groups are, for example, $C_1$-$C_4$ aminoalkyl groups; alkoxylated groups, such as the product marketed under the name "SILICONE COPOLYMER F-755" by SWS SILICONES and ABIL WAX® 2428, 2434 and 2440 by the company Evonik.

For example, the fatty substance in various embodiments may be chosen from compounds that are liquid or pasty at room temperature and at atmospheric pressure, such as a compound that is liquid at a temperature of 25° C. and at atmospheric pressure.

The fatty substance may be, for example, chosen from alkanes, fatty alcohols, esters of fatty acid, esters of fatty alcohol, hydrocarbons, silicones, non-silicone oils, non-silicone waxes, or mixtures thereof. The non-silicone oils may be selected from mineral, vegetable, synthetic oils, or mixtures thereof.

According to at least one embodiment, the fatty substance is chosen from liquid paraffin, polydecenes, liquid esters of fatty acids and of fatty alcohols, or mixtures thereof. In some embodiments, the fatty substance is chosen from alkanes, hydrocarbons, silicones, or mixtures thereof.

The liquid fatty substances are advantageously chosen from $C_6$-$C_{16}$ alkanes, non-silicone oils of plant, mineral or synthetic origin, liquid fatty alcohols, liquid fatty acids and liquid esters of a fatty acid and/or of a fatty alcohol, or mixtures thereof. In various embodiments, the liquid fatty substance comprises, consists essentially of, or consists of liquid petroleum jelly, $C_6$-$C_{16}$ alkanes, polydecenes, liquid esters of a fatty acid and/or of a fatty alcohol, liquid fatty alcohols, or mixtures thereof.

One liquid fatty substance for use according to the present disclosure is mineral oil, which may be commercially available from the supplier Sonneborn under the tradename Kaydol® Heavy White Mineral Oil, from the supplier Exxonmobil Chemical under the tradename Primol™ 352, from Sonneborn under the tradename Blandol, from Armedsa under the tradename Aemoil M-302CG, or from Exxonmobil Chemical under the tradename Marcol 82.

According to some embodiments, a hair color base according to the disclosure may include mineral oil and/or cetearyl alcohol as fatty substances. For example, the hair color base may include from about 2% to about 15% mineral oil, such as about 3% to about 7%, about 4% to about 6%, or about 5%, or such as about 8% to about 15%, about 10% to about 13%, or about 11% to about 12% mineral oil by weight, based on the total weight of the hair color base. The hair color base may include from about 2% to about 15% cetearyl alcohol, such as about 3% to about 7%, about 4% to about 6%, or about 5%, or such as about 8% to about 15%, about 10% to about 13%, or about 11% to about 12% cetearyl alcohol by weight, based on the total weight of the hair color base. In some embodiments, the hair color base may include approximately equal amounts of mineral oil and cetearyl alcohol.

In certain embodiments, the at least one fatty substance has a viscosity of about 50 mm$^2$/s or less at 40° C. (kinematic viscosity as measured by the ASTM D 445 method in units of mm$^2$/s at 40° C.). In other embodiments, the at least one fatty substance has a viscosity of greater than about 50 mm$^2$/s at 40° C., and may be chosen from oils such as mineral oil (kinematic viscosity as measured by the ASTM D445 method in units of mm$^2$/s at 40° C.).

Rheology Modifiers/Thickeners

The hair color base may optionally include at least one rheology modifier and/or thickener. Alternatively, one or more rheology modifiers and/or thickeners may be present in a separate composition that is mixed with the hair color base before use. In preferred embodiments, the hair color base includes at least one rheology modifier or thickening agent.

In at least some embodiments, the rheology modifier and/or thickener is an acrylic polymer. When present, the at least one acrylic polymer may, for example, be selected from crosslinked copolymers of (meth)acrylic acid and/or (C1-C6)alkyl esters and from acrylic associative polymers.

The expression "acrylic polymer" is understood, for purposes of the present disclosure, to mean a polymer that results from the polymerization of one or more monomers.

The acrylic polymer of the present disclosure may also belong to a group of compounds known as acrylic thickening polymers.

The expression "thickening polymer" is understood, for the purposes of the present disclosure, to mean a polymer having, in solution or in dispersion containing 1% by weight of active material in water or in ethanol at 25° C., a viscosity greater than 0.2 poise at a shear rate of 1 s$^{-1}$. The viscosity can be measured with a HAAKE RS600 viscometer from THERMO ELECTRON. This viscometer is a controlled-stress viscometer with cone-plate geometry (for example having a diameter of 60 mm).

As used herein, the term "(meth)acrylic acid" and "(meth) acrylate" are meant to include acrylic acid as well as the corresponding methyl derivatives of acrylic acid, and acrylate as well as the corresponding alkyl acrylates including methyl. For example, "(meth)acrylic acid" refers to acrylic acid and/or methacrylic acid, and "(meth)acrylate" refers to alkyl acrylate and/or alkyl methacrylate.

In certain embodiments, the acrylic polymer of the present disclosure is selected from crosslinked copolymers of methacrylic acid and of a C1-C6 alkyl ester wherein the C1-C6 alkyl ester is a C1-C6 alkyl acrylate.

Methacrylic acid may be present in amounts ranging from 20% to 80% by weight, more particularly from 25% to 70% by weight, such as from 35% to 65% by weight, relative to the total weight of the copolymer.

The alkyl acrylate may be present in amounts ranging from 15% to 80% by weight, such as from 25% to 75% by weight or from 35% to 65% by weight relative to the total weight of the copolymer. The alkyl acrylates may comprise, consist essentially of, or consist of methyl acrylate, ethyl acrylate, butyl acrylate, or mixtures thereof.

This copolymer may be partially or totally/substantially crosslinked with at least one standard polyethylenically unsaturated crosslinking agent, for instance polyalkenyl ethers of sucrose or of polyols, diallyl phthalates, divinylbenzene, allyl (meth)acrylate, ethylene glycol di(meth)acrylate, methylenebisacrylamide, trimethylolpropane tri(meth)acrylate, diallyl itaconate, diallyl fumarate, diallyl maleate, zinc (meth)acrylate, and castor oil or polyol derivatives manufactured from unsaturated carboxylic acids. The content of crosslinking agent generally ranges from 0.01% to 5% by weight, such as from 0.03% to 3% by weight or from 0.05% to 1% by weight, relative to the total weight of the copolymer.

In certain embodiments, the crosslinked copolymer of methacrylic acid and of a C1-C6 alkyl acrylate is slightly cross-linked. As used herein, the term "slightly crosslinked" refers to a partially crosslinked three-dimensional polymeric network.

In other certain embodiments, the crosslinked copolymer of methacrylic acid and of a C1-C6 alkyl acrylate is alkali-swellable. As used herein, the term "alkali-swellable" as it pertains to the acrylic polymer of the present disclosure refers to a polymer that when introduced to a solution, imparts little or no viscosity, but upon adjusting the pH to mildly acidic, neutral, or mildly basic conditions, a measurable increase in viscosity is observed, i.e., adding an alkali or neutralizing agent to a solution containing an alkali swellable polymer results in the development of viscosity.

The term "alkali-swellable" as used herein may also refer to the expansion of the polymer molecules upon neutralization as a result of charge repulsion of the anionic carboxylate groups of the polymer.

According to one form, the crosslinked copolymer of the invention may especially be in the form of a dispersion of particles in water.

Various exemplary useful acrylic polymers may be chosen from a crosslinked (meth)acrylic acid/ethyl acrylate copolymer, a cross-linked anionic acrylate polymer, or mixtures thereof.

According to some embodiments, the acrylic polymer of the present disclosure selected from a crosslinked (meth)acrylic acid/ethyl acrylate copolymer and a cross-linked anionic acrylate polymer copolymer may be in the form of a dispersion of polymer particles in water. The mean size of the copolymer particles in the dispersion generally ranges from 10 to 500 nm, such as from 20 to 200 nm or from 50 to 150 nm.

In certain embodiments, the crosslinked (meth)acrylic acid/ethyl acrylate copolymer is a crosslinked methacrylic acid/ethyl acrylate copolymer, also known as an acrylates copolymer in aqueous dispersion, an example of which is a slightly cross-linked, alkali-swellable acrylate polymer known by the INCI name acrylates copolymer and commercially available from the supplier Lubrizol, under the trade name Carbopol® Aqua SF-1 as an aqueous dispersion comprising about 30% by weight of total solids or active material. Carbopol® Aqua SF-1 has a carboxyl functionality in its protonated form. This copolymer belongs to a class of synthetic rheology modifiers that include carboxyl functional alkali-swellable and alkali-soluble thickeners (ASTs). These thickener polymers are prepared from the free-radical polymerization of acrylic acid alone or in combination with other ethylenically unsaturated monomers. The polymers can be synthesized by solvent/precipitation as well as emulsion polymerization techniques.

Other suitable crosslinked (meth)acrylic acid/ethyl acrylate copolymers may be chosen from a crosslinked copolymer of methacrylic acid and of ethyl acrylate as an aqueous dispersion containing 38% active material, commercially available from the company Coatex under the name Viscoatex™ 538C or a crosslinked copolymer of acrylic acid and of ethyl acrylate as an aqueous dispersion containing 28% active material, commercially available from the company Rohm and Haas and sold under the name Aculyn™ 33.

In other embodiments, the acrylic polymer of the present disclosure is a cross-linked anionic acrylate polymer. The cross-linked anionic acrylate polymer may be contained in an aqueous dispersion comprising about 32% by weight of total solids. Examples of the cross-linked anionic acrylate polymer of the present disclosure include, but are not limited to, the polymer known by the INCI name acrylates crosspolymer-4 and commercially available from the supplier Lubrizol, under the tradename Carbopol® Aqua SF-2, as an aqueous dispersion comprising about 32% by weight of total solids or active material. Acrylates Crosspolymer-4 may also be described as a copolymer of acrylic acid, methacrylic acid or one of its simple esters, crosslinked with trimethylolpropane triacrylate.

In certain other embodiments, the acrylic polymer of the present disclosure is selected from acrylic associative polymers, also known as acryic associative thickeners. The expression "associative thickener" is understood according to the invention to mean an amphiphilic thickener comprising both hydrophilic units and hydrophobic units, in particular comprising at least one C8-C30 fatty chain and at least one hydrophilic unit.

Acrylic associative thickeners that may be used according to the invention are acrylic associative polymers selected from: (i) nonionic amphiphilic polymers comprising at least one fatty chain and at least one hydrophilic unit; (ii) anionic amphiphilic polymers comprising at least one hydrophilic unit and at least one fatty-chain unit; (iii) cationic amphiphilic polymers comprising at least one hydrophilic unit and at least one fatty-chain unit; (iv) amphoteric amphiphilic polymers comprising at least one hydrophilic unit and at least one fatty-chain unit; or mixtures thereof, the fatty chains of (i)-(iv) containing from 10 to 30 carbon atoms.

Acrylic associative polymers may be chosen from acrylic anionic amphiphilic polymers such as those comprising at least one hydrophilic unit of unsaturated olefinic carboxylic acid type, and at least one hydrophobic unit of (C10-C30) alkyl ester of an unsaturated carboxylic acid type. They may be chosen from those in which the hydrophilic unit of unsaturated olefinic carboxylic acid type corresponds to the monomer of formula (II):

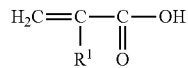

in which formula R1 denotes H or CH3 or C2H5, e.g. acrylic acid, methacrylic acid, or ethacrylic acid units, and the hydrophobic unit of which, of (C10-C30)alkyl ester of an unsaturated carboxylic acid type, corresponds to the monomer of formula (III):

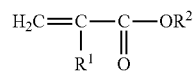

in which formula R1 denotes H or CH3 or C2H5 (e.g. acrylate, methacrylate, or ethacrylate units) and preferably H (acrylate units) or CH3 (methacrylate units), R2 denoting a C10-C30, for example a C12-C22, alkyl radical.

For example, (C10-C30) alkyl esters of unsaturated carboxylic acids according to the invention include lauryl acrylate, stearyl acrylate, decyl acrylate, isodecyl acrylate and dodecyl acrylate, and the corresponding methacrylates, lauryl methacrylate, stearyl methacrylate, decyl methacrylate, isodecyl methacrylate, dodecyl methacrylate, or mixtures thereof.

Anionic amphiphilic polymers of this type are disclosed and prepared, for example, according to the U.S. Pat. No. 3,915,921 and U.S. Pat. No. 4,509,949.

The anionic amphiphilic polymers that can be used in the context of the present disclosure may more particularly denote polymers formed from a mixture of monomers comprising:
(i) acrylic acid and one or more esters of formula (IV):

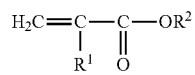

in which R1 denotes H or CH3, R2 denoting an alkyl radical having from 12 to 22 carbon atoms, and a crosslinking agent, such as, for example, those constituted of from 95% to 60% by weight of acrylic acid (hydrophilic unit), 4% to 40% by weight of C10-C30 alkyl acrylate (hydrophobic unit), and 0% to 6% by weight of crosslinking polymerizable monomer, or 98% to 96% by weight of acrylic acid (hydrophilic unit), 1% to 4% by weight of C10-C30 alkyl acrylate (hydrophobic unit) and 0.1% to 0.6% by weight of cross-linking polymerizable monomer; and
(ii) essentially acrylic acid and lauryl methacrylate, such as the product formed from 66% by weight of acrylic acid and 34% by weight of lauryl methacrylate.

The crosslinking agent may be a monomer containing a

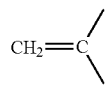

group with at least one other polymerizable group whose unsaturated bonds are not conjugated relative to one another. Mention may be made in particular of polyallyl ethers such as, in particular, polyallyl sucrose and polyallyl pentaerythritol.

Among said polymers above, the products sold by the company Goodrich under the trade names Pemulen™ TR1, Pemulen™ TR2, Carbopol® 1382, and the product sold by the company Coatex under the name Coatex SX®, may be chosen.

Thus, in some embodiments, the acrylic polymer of the present disclosure is an acrylate polymer contained in an aqueous dispersion comprising about 30% by weight of active material. This acrylate polymer may be slightly cross-linked and alkali-swellable.

In other embodiments, the acrylic polymer of the present disclosure is a cross-linked anionic acrylate polymer contained in an aqueous dispersion comprising about 32% by weight of active material.

In yet other embodiments, the acrylic polymer of the present disclosure is comprises, consists essentially of, or consists of a slightly cross-linked, alkali-swellable acrylate polymer contained in an aqueous dispersion comprising about 30% by weight of active material, a cross-linked anionic acrylate polymer contained in an aqueous dispersion from comprising about 32% by weight of active material, or mixtures thereof.

In some other embodiments, the acrylic polymer of the present disclosure is chosen from acrylic associative polymers, in particular, acrylic anionic amphiphilic polymers which can be selected from those comprising at least one hydrophilic unit of unsaturated olefinic carboxylic acid type, and at least one hydrophobic unit of (C10-C30) alkyl ester of an unsaturated carboxylic acid type.

In certain embodiments, the at least one acrylic polymer of the present disclosure may be a carbomer (4% solution) employed in an amount of from about 0.2% to about 1% by weight, such as from about 0.3% to about 0.0% by weight, from about 0.4% to about 0.8% by weight, or from about 0.5% to about 0.7%, such as at about 0.6% by weight, based on the total weight of the hair color base.

Thickening agents and rheology modifying polymers other than the above-described acrylic polymers may be added, for example polymeric thickeners and/or non-polymeric thickeners. The polymeric thickener can be chosen from ionic or non-ionic, associative or non-associative polymers. Exemplary polymeric thickeners include various native gums. Representative non-polymeric thickening agents include oxyethylenated molecules and especially ethoxylated alkyl or acyl derivatives of polyols. These polymers can be modified physically or chemically.

When present, the total amount of rheology modifiers and/or thickening agents may be used in an amount of greater than 0% to about 15% by weight, such as from about 0.1% to about 10% by weight, or from about 1% to about 5% by weight, based on the total weight of the hair color base.

Cationic Polymers

The hair color base according to the present disclosure can also comprise at least one cationic polymer. The cationic polymer may be chosen from cationic associative polymers comprising, in their structure, a pendent or terminal hydrophobic chain, for example of alkyl or alkenyl type, containing from 10 to 30 carbon atoms.

The at least one cationic polymer of the compositions can also be chosen from the following:

(1) homopolymers and copolymers derived from acrylic or methacrylic esters or amides, examples of which are: copolymers of acrylamide and of dimethylaminoethyl acrylate quaternized with dimethyl sulfate or with a dimethyl halide, such as the product sold under the name HERCOFLOC by the company Hercules; the copolymers of acrylamide and of methacryloyloxyethyltrimethyl-ammonium chloride described, for example, in EP 80 976 and sold under the name BINA QUAT P 100 by the company Ciba Geigy; the copolymer of acrylamide and of methacryloyloxyethyltrimethylammonium methosulfate sold under the name RETEN by the company Hercules; quaternized or non-quaternized vinylpyrrolidone/dialkylaminoalkyl acrylate or acrylate copolymers, such as the products sold under the name GAFQUAT by the company ISP, for instance GAFQUAT 734 or GAFQUAT 755, or alternatively the products known as COPOLYMER 845, 958, and 937, dimethylaminoethyl acrylate/vinylcaprolactam/vinylpyrrolidone terpolymers, such as the product sold under the name GAFFIX VC 713 by the company ISP; vinylpyrrolidone/methacrylamidopropyldimethylamine copolymers sold, for example, under the name STYLEZE CC 10 by ISP; quaternized vinylpyrrolidone/dimethylaminopropylmethacrylamide copolymers such as the product sold under the name GAFQUAT HS 100 by the company ISP, and crosslinked polymers of methacryloyloxy($C_1$-$C_4$)alkyltri($C_1$-$C_4$)alkylammonium salts such as the polymers obtained by homopolymerization of dimethylaminoethyl acrylate quaternized with methyl chloride, or by copolymerization of acrylamide with dimethylaminoethyl acrylate quaternized with methyl chloride, the homo- or copolymerization being followed by crosslinking with a compound containing olefinic unsaturation, such as methylenebisacrylamide.

In at least one embodiment, a crosslinked acrylamide/methacryloyloxyethyltrimethylammonium chloride copolymer (20/80 by weight) in the form of a dispersion containing 50% by weight of the copolymer in mineral oil can be used. This dispersion is sold under the name SALCARE® SC 92 by the company Ciba. In some embodiments, a crosslinked methacryloyloxyethyltrimethylammonium chloride homopolymer containing about 50% by weight of the homopolymer in mineral oil or in a liquid ester can be used. These dispersions are sold under the names SALCARE® SC 95 and SALCARE® SC 96 by the company Ciba.

Other examples are cellulose ether derivatives comprising quaternary ammonium groups, such as the polymers sold under the names JR (JR 400, JR 125, JR 30M) or LR (LR 400, LR 30M) by the company Union Carbide Corporation.

(2) Copolymers of cellulose or cellulose derivatives grafted with a water-soluble quaternary ammonium monomer, such as hydroxymethyl-, hydroxyethyl- or hydroxypropylcelluloses grafted, for instance, with a methacryloylethyltrimethylammonium, methacrylamidopropyltrimethylammonium, or dimethyldiallylammonium salt. These are sold under the name CELQUAT L 200 and CELQUAT H 100 by the company National Starch.

(3) Non-cellulose cationic polysaccharides, such as guar gums containing trialkylammonium cationic groups. Such products are sold, for example, under the trade names JAGUAR C13S, JAGUAR C15, JAGUAR C17 and JAGUAR C162 by the company Meyhall.

(4) Polymers of piperazinyl units and of divalent alkylene or hydroxyalkylene radicals.

(5) Water-soluble polyamino amides prepared, for example, by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in an amount ranging from 0.025 to 0.35 mol per amine group of the polyamino amide; these polyamino amides can be alkylated or, if they contain at least one tertiary amine function, they can be quaternized. Exemplary mention may be made of the adipic acid/dimethylaminohydroxypropyl/diethylenetriamine polymers sold under the name CARTARETINE F, F4 or F8 by the company Sandoz.

(6) The polymers obtained by reaction of at least one polyalkylene polyamine containing two primary amine groups and at least one secondary amine group with a dicarboxylic acid chosen from diglycolic acid and saturated $C_3$-$C_8$ aliphatic dicarboxylic acids. The molar ratio between the polyalkylene polyamine and the dicarboxylic acid ranges from 0.8:1 to 1.4:1; the polyamino amide resulting therefrom is reacted with epichlorohydrin in a molar ratio of epichlorohydrin relative to the secondary amine group of the polyamino amide ranging from 0.5:1 to 1.8:1. Polymers of this type are sold, for example, under the name HERCOSETT 57, PD 170 or DELSETTE 101 by the company Hercules.

(7) Cyclopolymers of alkyldiallylamine and of dialkyldiallylammonium, such as for example: dimethyldiallylammonium chloride homopolymer sold under the name MERQUAT® 100 and MERQUAT® 280 by the company Nalco (and its homologues of low weight-average molecular mass) and the copolymers of diallyldimethylammonium chloride and of acrylamide, sold under the name MERQUAT® 550.

(8) Quaternary diammonium polymers.

(9) Polyquaternary ammonium polymers; examples that may be mentioned include the products MIRAPOL A 15, MIRAPOL AD1, MIRAPOL AZ1 and MIRAPOL 175 sold by the company Miranol.

(10) Quaternary polymers of vinylpyrrolidone and of vinylimidazole, for instance the products sold under the names LUVIQUAT FC 905, FC 550 and FC 370 by the company BASF.

(11) Vinylamide homopolymers or copolymers, such as partially hydrolysed vinylamide homopolymers such as poly(vinylamine/vinylamide)s.

(12) Cationic polyurethane derivatives, for example those of elastic nature formed from the reaction of: (a1) at least one cationic unit resulting from at least one tertiary or quaternary amine bearing at least two reactive functions containing labile hydrogen; (a2) at least one mixture of at least two different nonionic units bearing at least two reactive functions containing labile hydrogen, for instance chosen from hydroxyl groups, primary or secondary amine groups, and thiol groups; and (b) at least one compound comprising at least two isocyanate functions.

(13) Other cationic polymers that may be used in the context of the disclosure include, for example, cationic proteins or cationic protein hydrolysates, polyalkyleneimines, such as polyethyleneimines, polymers containing vinylpyridine or vinylpyridinium units, and chitin derivatives.

Particularly useful cationic polymers in the present disclosure include, but are not limited to, polyquaternium 4, polyquaternium 6, polyquaternium 7, polyquaternium 10, polyquaternium 11, polyquaternium 16, polyquaternium 22, polyquaternium 28, polyquaternium 32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, and guar hydroxypropyltrimonium chloride.

Useful cationic polymers include POLYMER JR-125, POLYMER JR-400, Polymer JR-30M hydroxyethyl cellulosic polymers (polyquaternium 10) available from AMERCHOL; JAGUAR C® 13-S, guar hydroxypropyltrimonium chloride, available from Rhodia; and MERQUAT® 100 and 280, a dimethyl dialkyl ammonium chloride (polyquaternium 6) available from Nalco.

When present, the total amount of cationic polymer may range from greater than 0% to about 5%, such as from about 0.25% to about 3% by weight, or from about 0.5% to about 1.5% by weight, based on the total weight of the hair color base.

Auxiliary Components

The hair color base according to the disclosure can comprise any auxiliary or additional component suitable for use in cosmetic compositions, and in particular suitable for hair coloring or lightening compositions. Alternatively, one or more auxiliary or additional component may be present in a separate composition that is mixed with the hair color base before use.

Such components may include, but are not limited to, silicone compounds, thickening agents or rheology modifiers other than described above, anionic, cationic, nonionic, amphoteric or zwitterionic surfactants or mixtures thereof, anionic, cationic, nonionic, amphoteric or zwitterionic polymers or mixtures, film forming agents or polymers, humectants and moisturizing agents, fatty substances, emulsifying agents other than fatty substances, fillers, structuring agents, propellants, shine agents, conditioning agents, antioxidants or reducing agents, penetrants, sequestrants, fragrances, buffers, dispersants, conditioning agents, for instance volatile or non-volatile, modified or unmodified silicones, ceramides, preserving agents, opacifiers, sunscreen agents, pH adjusters, and antistatic agents. Acids, for example citric acid, can affect the pH of the system resulting in loss of lift. As such, optional auxiliary or additional components will be chosen so as to minimize any detrimental effect to the advantages of the hair color bases and compositions described herein.

According to some embodiments the antistatic agent may include a hexadimethrine chloride polymer. In various embodiments, the sequestering agents may include ethylenediaminetetraacetic acid (EDTA) or its conjugate base.

The components of the hair color base may be chosen to maintain an alkaline pH. Thus, according to one embodiment, the pH of the hair color base ranges from about 8 to about 11. In some embodiments, the pH of the hair color base may range from about 8.5 to about 10, such as from about 8.5 to about 9.5, about 9.0 to about 9.5, or about 9.2 to about 9.5. When additional components such as a colorant is present, the pH of the hair color base may vary within the above range according to the type of colorant included therein.

Typically, the foregoing optional components may be present in amounts up to about 25%, such as about 0.1% to about 20%, or about 1% to about 10%, by weight of the hair color base, when present, although different amounts are also contemplated.

Hair Color Altering Composition

The disclosure also relates to compositions for altering the color of hair. The hair color altering compositions comprise a hair color base according to the disclosure and an oxidizing component, and optionally additional components traditionally used in hair color altering compositions.

In various embodiments, hair color altering compositions may be prepared by mixing a hair color base according to the disclosure with an oxidizing component. For example, a hair color base according to the disclosure may be mixed with an oxidizing component in a ratio of hair color base:oxidizing component ranging from about 1:1 to about 1:10, such as from about 1:1 to about 1:4, from about 1:1 to about 1:3, or from about 1:1 to about 1:2. The mixing ratio of hair color base to oxidizing component may be, for example, about 1:1, about 1:2, about 1:3, or about 1:4.

Oxidizing Component

The hair color composition according to the disclosure comprises at least one oxidizing component. The oxidizing component may be an oxidizing agent, or may be a composition comprising an oxidizing agent ("oxidizing composition"), which terms are used interchangeably in some instances herein, without intending to be limiting.

Oxidizing Agents

The oxidizing agent may be, for example, chosen from peroxides, persulfates, perborates, percarbonates, alkali metal bromates, ferricyanides, peroxygenated salts, or a mixture thereof. Oxidizing agents that may also be used include at least one redox enzyme such as laccases, peroxidases, and 2-electron oxidoreductases, such as uricase, where appropriate in the presence of their respective donor or co-factor. Oxygen in the air may also be an oxidizing component.

In certain embodiments, the oxidizing agent is hydrogen peroxide. In various embodiments the hydrogen peroxide may be present in an aqueous solution whose titer may range from 1 to 40 volumes, such as from 5 to 40 volumes, from 5 to 30 volumes, or from 5 to 20 volumes. In certain embodiments, the oxidizing component is an aqueous 10 V, 20 V, 30 V, or 40 V hydrogen peroxide oxidizing composition.

In other embodiments, the oxidizing agent is a persulfate and/or a monopersulfate such as, for example, potassium persulfate, sodium persulfate, ammonium persulfate, as well as mixtures thereof. In some embodiments, the oxidizing agents are chosen from hydrogen peroxide, potassium persulfate, sodium persulfate, or mixtures thereof.

Oxidizing Compositions

When the oxidizing component is an oxidizing composition, the oxidizing agent may, in various embodiments, be present in an amount of from about 0.05% to about 50% by weight, such as from about 0.1% to about 30% by weight, from about 0.1% to about 20% by weight, about 1% to about 20%, about 1% to about 15%, about 1% to about 12%, about 3% to about 20%, about 3% to about 15%, about 3% to about 12%, about 5% to about 20%, about 5% to about 15%, about 5% to about 12%, about 7% to about 20%, about 7% to about 15%, about 7% to about 12%, about 9% to about 20%, about 9% to about 15%, or about 9% to about 12% by weight, based on the total weight of the oxidizing composition. The total amount of oxidizing agent in the oxidizing composition is preferably at least about 7%, at least about 8%, at least about 9%, at least about 10%, at least about 11%, or at least about 11.5%, such as at 8% to about 12%, about 9% to about 12%, about 10% to about 12%, about 11% to about 12%, or is about 9%, about 10%, about 11%, or about 12%, or about 1% to about 10% by weight, based on the total weight of the oxidizing composition.

The oxidizing composition can contain at least one solvent, for example water, organic solvents, or mixtures thereof. Suitable organic solvents for use in the oxidizing composition, alone or in mixture with water, include but are not limited to ethanol, isopropyl alcohol, propanol, benzyl alcohol, phenyl ethyl alcohol, glycols and glycol ethers, such as propylene glycol, hexylene glycol, ethylene glycol monomethyl, monoethyl or monobutyl ether, propylene glycol and its ethers, such as propylene glycol monomethyl ether, butylene glycol, dipropylene glycol, diethylene glycol alkyl ethers, such as diethylene glycol monoethyl ether and monobutyl ether, ethylene glycol, propylene glycol, butylene glycol, hexylene glycol, propane diol, glycerin, hydrocarbons such as straight chain hydrocarbons, mineral oil, polybutene, hydrogenated polyisobutene, hydrogenated polydecene, polydecene, squalane, petrolatum, isoparaffins, or mixtures thereof.

The organic solvents for use according to the present disclosure can be volatile or non-volatile compounds. The total amount of organic solvent may, for example, range from about 0.5% to about 70% by weight, such as from about 2% to about 60% by weight, such as from about 5 to about 50% by weight, relative to the total weight of the oxidizing composition.

The oxidizing compositions may optionally include other components typically used in oxidizing compositions, such as, for example, rheology modifying or thickening agents, chelants, fatty substances, ceramides, pH adjusting agents, preservatives, fragrances, surfactants, etc.

The oxidizing composition may be in the form of a powder, gel, liquid, foam, lotion, cream, mousse, or emulsion. In certain embodiments the oxidizing composition is aqueous and is in the form of a liquid, cream, or emulsion. In other embodiments, the oxidizing composition is anhydrous or substantially anhydrous.

The pH of the oxidizing composition can range from about 2 to about 12, such as from about 6 to about 11, and it may be adjusted to the desired value using acidifying/alkalizing agents that are well known in the art. In certain embodiments, the pH of the oxidizing composition is above 7. In other embodiments the pH of the oxidizing composition may be below 7, such as from about 2 to about 6, or from about 3 to about 5.

Additional Components

The hair color altering compositions may optionally comprise any of the additional components described above for the hair color base compositions, including, but not limited to, colorants, solvents, nonionic surfactants, fatty substances, rheology modifiers, cationic polymers, and/or auxiliary components. Such additional components may be present in the hair color altering compositions as part of the oxidizing component or hair color altering compositions, or may be present in the hair color altering compositions as part of a hair color base that is added to the hair color altering composition.

The amounts of each such additional component may be present in the hair color altering composition in the same amounts as described herein when present in the emulsion or cream hair color base, or in higher or lower amounts. For example, each of the expressly described alkoxylated fatty alcohols, fatty acids, fatty alcohols other than alkoxylated fatty alcohols, ammonium hydroxide, ammonium bicarbonate, monoethanolamine, colorant compounds, thickening agents, solvents, etc., may be present in approximately 1/2 the amount(s) as described for the emulsion or cream hair color base when the hair color altering composition is prepared by mixing a hair color base composition with an oxidizing component at a ratio of (buffer system or hair color base comprising the buffer system):oxidizing component of about 1:1, may be present in ⅓ the amount(s) described for the hair color base (mixing ratio of about 1:2), may be present in ¼ the amount(s) described for the hair color base (mixing ratio of about 1:3), may be present in ⅕ the amount(s) described for the hair color base (mixing ratio of about 1:4), and so on.

The pH of the hair color altering composition may, in at least certain embodiments, be the same or substantially the same as the pH of the emulsion or cream hair color base, for example prior to mixing the hair color base and oxidizing component. In some embodiments, the pH of the hair color altering composition may preferably range from about 8.5 to about 10, or such as from about 8.5 to about 9.5, about 9.0 to about 9.5, or about 9.2 to about 9.5. In further embodiments, the pH of the hair color altering composition may be greater than 7, such as greater than about 8, for example may range from about 8 to about 11.5, from about 8.5 to about 11, from about 9 to about 10.5, or from about 9.5 to about 10.5, most preferably from about 9.5 to about 10.25 or from about 9.75 to about 10. When a colorant is present, the pH of hair color altering composition may vary within the above range according to the type of colorant included therein. If the pH is below about 8.5, the hair color altering composition may produce an insufficient amount of lift or alteration of color. If the pH is above about 10, the hair color altering composition may unnecessarily damage hair.

The hair color altering compositions can, in some embodiments, be prepared by combining an emulsion or cream hair color base according to the disclosure with an oxidizing component. In yet further embodiments, the hair color altering compositions can be prepared by combining (i) an emulsion or cream hair color base according to the disclosure, (ii) a composition comprising at least one component chosen from colorants, solvents, nonionic surfactants, fatty substances, rheology modifiers, cationic polymers, and auxiliary components as described herein, and (iii) an oxidizing component.

In yet further embodiments, the hair color altering compositions can be prepared by combining an emulsion or cream hair color base according to the disclosure with an oxidizing composition comprising hydrogen peroxide. In further embodiments, the hair color altering compositions can be prepared by combining (i) an emulsion or cream hair color base according to the disclosure, (ii) a composition comprising at least one component chosen from colorants, solvents, nonionic surfactants, fatty substances, rheology modifiers, cationic polymers, and auxiliary components as described herein, and (iii) an oxidizing composition comprising hydrogen peroxide.

The hair color altering compositions are generally creamy in form, and are easy to apply.

In some embodiments, hair color altering compositions according to the disclosure comprise at least one alkoxylated fatty alcohol, at least one fatty acid, at least one fatty alcohol other than the alkoxylated fatty alcohol, ammonium hydroxide, ammonium bicarbonate, at least one oxidizing component, at least one colorant compound, at least one solvent, optionally monoethanolamine, and optionally at least one other component suitable for use in cosmetic compositions, and in particular for hair coloring or lightening compositions, for example at least one thickening agent.

According to various embodiments, hair color altering compositions comprise, based on the total weight of the hair color altering composition, from about 10% to about 30%, preferably from about 10% to about 28%, about 10% to about 25%, about 10% to about 22%, about 12% to about 30%, about 12% to about 28%, about 12% to about 25%, about 12% to about 22%, about 15% to about 30%, about 15% to about 28%, about 15% to about 25%, about 15% to about 22%, about 18% to about 30%, about 18% to about 28%, about 18% to about 25%, or about 18% to about 22% of at least one alkoxylated fatty alcohol; from about 1% to about 8%, preferably from about 1% to about 7%, about 1% to about 6%, about 1% to about 5%, about 1% to about 4%, about 1% to about 3%, about 1% to about 2%, about 2% to about 8%, about 2% to about 7%, about 2% to about 6%, about 2% to about 5%, about 2% to about 4%, about 2% to about 3%, about 3% to about 8%, about 3% to about 7%, about 3% to about 6%, about 3% to about 5%, about 3% to about 4%, about 4% to about 8%, about 4% to about 7%, about 4% to about 6%, or about 4% to about 5% of at least one fatty acid; at least about 8%, such as at least about 9%, or at least about 10%, preferably from about 8% to about 20%, about 8% to about 18%, about 8% to about 15%, about 8% to about 13%, about 8% to about 12%, about 9% to about 20%, about 9% to about 18%, about 9% to about 15%, about 9% to about 13%, about 9% to about 12%, about 10% to about 20%, about 10% to about 18%, about 10% to about 15%, about 10% to about 13%, about 10% to about 12%, about 11% to about 20%, about 11% to about 18%, about 11% to about 15%, about 11% to about 13%, or about 11% to about 12% of at least one fatty alcohol other than the alkoxylated fatty alcohol; from about 0.1% to about 10%, preferably from about 1% to about 6%, about 1.5% to about 5%, about 2% to about 4.75%, about 2.5% to about 4.5%, or about 2.5% to about 4% of ammonium hydroxide; from about 0.1% to about 5%, preferably from about 0.1% to about 2.5%, about 0.2% to about 2.25%, about 0.3% to about 2%, about 0.4% to about 1.75%, or about 0.5% to about 1.5% of ammonium bicarbonate; and optionally, from about 0.1% to about 5%, preferably from about 0.5% to about 2.5% of monoethanolamine; at least one oxidizing component; optionally at least one colorant compound; and optionally at least one thickening agent, wherein the molar ratio of ammonium hydroxide to ammonium bicarbonate is greater than about 1.2, preferably greater than about 1.5, greater than about 1.55, greater than about 1.6, greater than about 1.65, greater than about 1.7, greater than about 1.75, greater than about 1.8, greater than about 1.85, greater than about 1.9, greater than about 1.95, greater than about 2, greater than about 2.5, greater than about 3.0, or greater than about 3.5, for example ranges from about 1.5 to about 4, preferably from about 1.5 to about 3.75, from about 1.5 to about 3.5, from about 1.5 to about 3, or from about 1.5 to about 2.5, more preferably from about 1.5 to about 2 or from about 1.5 to about 1.75, most preferably from about 1.65 to about 1.75, or is about 1.65, about 1.7, or about 1.75.

According to further embodiments, hair color altering compositions comprise, based on the total weight of the hair color altering composition, from about 5% to about 15%, preferably from about 5% to about 14%, about 5% to about 13%, about 5% to about 12%, about 6% to about 15%, about 6% to about 14%, about 6% to about 13%, about 6% to about 12%, about 7% to about 15%, about 7% to about 14%, about 7% to about 13%, about 7% to about 12%, about 8% to about 15%, about 8% to about 14%, about 8% to about 13%, or about 8% to about 12% of at least one alkoxylated fatty alcohol; from about 0.5% to about 4%, preferably from about 0.5% to about 3.5%, about 0.5% to about 3%, about 0.5% to about 2.5%, about 0.5% to about 2%, about 0.5% to about 1.5%, about 0.5% to about 1%, about 1% to about 4%, about 1% to about 3.5%, about 1% to about 3%, about 1% to about 2.5%, about 1% to about 2%, about 1% to about 1.5%, about 1.5% to about 4%, about 1.5% to about 3.5%, about 1.5% to about 3%, about 1.5% to about 2.5%, about 1.5% to about 2%, about 2% to about 4%, about 2% to about 3.5%, about 2% to about 3%, or about 2% to about 2.5% of at least one fatty acid; at least about 4%, such as at least about 4.5%, or at least about 5%, preferably from about 4% to about 10%, about 4% to about 9%, about 4% to about 7.5%, about 4% to about 6.5%, about 4% to about 6%, about 4.5% to about 10%, about 4.5% to about 9%, about 4.5% to about 7.5%, about 4.5% to about 6.5%, about 4.5% to about 6%, about 5% to about 10%, about 5% to about 9%, about 5% to about 7.5%, about 5% to about 6.5%, about 5% to about 6%, about 5.5% to about 10%, about 5.5% to about 9%, about 5.5% to about 7.5%, about 5.5% to about 6.5%, or about 5.5% to about 6% of at least one fatty alcohol other than the alkoxylated fatty alcohol; from about 0.05% to about 5%, preferably from about 0.5% to about 3%, about 0.75% to about 2.5%, about 1% to about 2.5%, about 1.25% to about 2.25%, or about 1.25% to about 2% of ammonium hydroxide; from about 0.05% to about 2.5%, preferably from about 0.05% to about 1.25%, about 0.1% to about 1.25%, about 0.1% to about 1%, about 0.2% to about 1%, or about 0.25% to about 0.75% of ammonium bicarbonate; and optionally, from about 0.05% to about 2.5%, preferably from about 0.25% to about 1.25% of monoethanolamine; at least one oxidizing component; optionally at least one colorant compound; and optionally at least one thickening agent, wherein the molar ratio of ammonium hydroxide to ammonium bicarbonate is greater than about 1.2, preferably greater than about 1.5, greater than about 1.55, greater than about 1.6, greater than about 1.65, greater than about 1.7, greater than about 1.75, greater than about 1.8, greater than about 1.85, greater than about 1.9, greater than about 1.95, greater than about 2, greater than about 2.5, greater than about 3.0, or greater than about 3.5, for example ranges from about 1.5 to about 4, preferably from about 1.5 to about 3.75, from about 1.5 to about 3.5, from about 1.5 to about 3, or from about 1.5 to about 2.5, more preferably from about 1.5 to about 2 or from about 1.5 to about 1.75, most preferably from about 1.65 to about 1.75, or is about 1.65, about 1.7, or about 1.75.

For example, the hair color altering compositions may comprise, based on the total weight of the hair color altering composition, from about 15% to about 25%, preferably from about 16% to about 24%, about 17% to about 23%, or about 18% to about 22% of at least one alkoxylated fatty alcohol;

from about 1% to about 8%, preferably from about 1% to about 6%, about 2% to about 8%, about 2% to about 6%, or about 2% to about 5% of at least one fatty acid; at least about 8%, such as at least about 9%, or at least about 10%, preferably from about 8% to about 15%, about 9% to about 15%, or about 10% to about 15% of at least one fatty alcohol other than the alkoxylated fatty alcohol; from about 1% to about 6%, about 2% to about 5%, or about 2.5% to about 4.25% of ammonium hydroxide; from about 0.1% to about 3%, preferably from about 0.25% to about 2.5%, about 0.4% to about 2%, or about 0.5% to about 1.5% of ammonium bicarbonate; from about 0.1% to about 2.5%, preferably from about 0.5% to about 1.5% of monoethanolamine; at least one oxidizing component; at least one colorant compound chosen from oxidative dyes and precursors; and at least one thickening agent, wherein the molar ratio of ammonium hydroxide to ammonium bicarbonate is greater than about 1.5, for example ranges from about 1.5 to about 4, preferably from about 1.5 to about 3.75, from about 1.5 to about 3.5, from about 1.5 to about 3, or from about 1.5 to about 2.5, more preferably from about 1.5 to about 2 or from about 1.5 to about 1.75, most preferably from about 1.65 to about 1.75, or is about 1.65, about 1.7, or about 1.75.

In further exemplary and non-limiting embodiments, the hair color altering compositions may comprise, based on the total weight of the hair color altering composition, from about 7.5% to about 12.5%, preferably from about 8% to about 12%, about 8.5% to about 11.5%, or about 9% to about 11% of at least one alkoxylated fatty alcohol; from about 0.5% to about 4%, preferably from about 0.5% to about 3%, about 1% to about 4%, about 1% to about 3%, or about 1% to about 2.5% of at least one fatty acid; at least about 4%, such as at least about 4.5%, or at least about 5%, preferably from about 4% to about 7.5%, about 4.5% to about 7.5%, or about 5% to about 7.5% of at least one fatty alcohol other than the alkoxylated fatty alcohol; from about 0.5% to about 3%, about 1% to about 2.5%, or about 1.25% to about 2% of ammonium hydroxide; from about 0.05% to about 1.5%, preferably from about 0.2% to about 1.25%, about 0.2% to about 1%, or about 0.25% to about 0.75% of ammonium bicarbonate; from about 0.05% to about 1.25%, preferably from about 0.25% to about 0.75% of monoethanolamine; at least one oxidizing component; at least one colorant compound chosen from oxidative dyes and precursors; and at least one thickening agent, wherein the molar ratio of ammonium hydroxide to ammonium bicarbonate is greater than about 1.5, for example ranges from about 1.5 to about 4, preferably from about 1.5 to about 3.75, from about 1.5 to about 3.5, from about 1.5 to about 3, or from about 1.5 to about 2.5, more preferably from about 1.5 to about 2 or from about 1.5 to about 1.75, most preferably from about 1.65 to about 1.75, or is about 1.65, about 1.7, or about 1.75.

As yet a further example, the hair color altering compositions may comprise, based on the total weight of the hair color altering composition, from about 5% to about 8.5%, preferably from about 5% to about 8%, about 5.5% to about 7.75%, or about 6% to about 7.5% of at least one alkoxylated fatty alcohol; from about 0.3% to about 3%, preferably from about 0.3% to about 2%, about 0.5% to about 3%, about 0.5% to about 2%, or about 0.5% to about 1.75% of at least one fatty acid; at least about 2.5%, such as at least about 3%, or at least about 3.5%, preferably from about 2.5% to about 5%, about 3% to about 5%, or about 3.5% to about 5% of at least one fatty alcohol other than the alkoxylated fatty alcohol; from about 0.3% to about 2%, about 0.3% to about 1.75%, or about 0.75% to about 1.5% of ammonium hydroxide; from about 0.03% to about 1%, preferably from about 0.1% to about 1%, about 0.15% to about 0.75%, or about 0.15% to about 0.5% of ammonium bicarbonate; from about 0.03% to about 1.75%, preferably from about 0.15% to about 0.5% of monoethanolamine; at least one oxidizing component; at least one colorant compound chosen from oxidative dyes and precursors; and at least one thickening agent, wherein the molar ratio of ammonium hydroxide to ammonium bicarbonate is greater than about 1.5, for example ranges from about 1.5 to about 4, preferably from about 1.5 to about 3.75, from about 1.5 to about 3.5, from about 1.5 to about 3, or from about 1.5 to about 2.5, more preferably from about 1.5 to about 2 or from about 1.5 to about 1.75, most preferably from about 1.65 to about 1.75, or is about 1.65, about 1.7, or about 1.75.

As a still further embodiment, the hair color altering compositions may comprise, based on the total weight of the hair color altering composition, from about 3.75% to about 6.25%, preferably from about 4% to about 6%, about 4.25% to about 5.75%, or about 4.5% to about 5.5% of at least one alkoxylated fatty alcohol; from about 0.25% to about 2%, preferably from about 0.25% to about 1.5%, about 0.5% to about 2%, about 0.5% to about 1.5%, or about 0.5% to about 1.25% of at least one fatty acid; at least about 2%, such as at least about 2.25%, or at least about 2.5%, preferably from about 2% to about 3.75%, about 2.25% to about 3.75%, or about 2.5% to about 3.75% of at least one fatty alcohol other than the alkoxylated fatty alcohol; from about 0.5% to about 1.5%, about 0.5% to about 1.25%, or about 0.6% to about 1.4% of ammonium hydroxide; from about 0.025% to about 0.75%, preferably from about 0.06% to about 0.63%, about 0.1% to about 0.5%, or about 0.1% to about 0.38% of ammonium bicarbonate; from about 0.025% to about 0.38%, preferably from about 0.1% to about 0.38% of monoethanolamine; at least one oxidizing component; at least one colorant compound chosen from oxidative dyes and precursors; and at least one thickening agent, wherein the molar ratio of ammonium hydroxide to ammonium bicarbonate is greater than about 1.5, for example ranges from about 1.5 to about 4, preferably from about 1.5 to about 3.75, from about 1.5 to about 3.5, from about 1.5 to about 3, or from about 1.5 to about 2.5, more preferably from about 1.5 to about 2 or from about 1.5 to about 1.75, most preferably from about 1.65 to about 1.75, or is about 1.65, about 1.7, or about 1.75.

For example, the hair color altering composition may include from about 10% to about 30% of at least one alkoxylated fatty alcohol; from about 2% to about 5% of at least one fatty acid; at least about 10% of at least one fatty alcohol other than the alkoxylated fatty alcohol; from about 3% to about 4.5% of ammonium hydroxide; from about 0.1% to about 2% of ammonium bicarbonate; from about 0.1% to about 2.5% of monoethanolamine; at least one oxidizing component; at least one colorant compound chosen from oxidative dyes and precursors; and at least one thickening agent, wherein the molar ratio of ammonium hydroxide to ammonium bicarbonate is greater than about 1.5, for example ranges from about 1.5 to about 4, preferably from about 1.5 to about 3.75, from about 1.5 to about 3.5, from about 1.5 to about 3, or from about 1.5 to about 2.5, more preferably from about 1.5 to about 2 or from about 1.5 to about 1.75, most preferably from about 1.65 to about 1.75, or is about 1.65, about 1.7, or about 1.75.

In a further example, the hair color altering composition may include from about 5% to about 15% of at least one alkoxylated fatty alcohol; from about 1% to about 2.5% of at least one fatty acid; at least about 5% of at least one fatty alcohol other than the alkoxylated fatty alcohol; from about 1.5% to about 2.25% of ammonium hydroxide; from about 0.05% to about 1% of ammonium bicarbonate; from about 0.05% to about 1.25% of monoethanolamine; at least one oxidizing component; at least one colorant compound chosen from oxidative dyes and precursors; and at least one thickening agent, wherein the molar ratio of ammonium hydroxide to ammonium bicarbonate is greater than about 1.5, for example ranges from about 1.5 to about 4, preferably from about 1.5 to about 3.75, from about 1.5 to about 3.5, from about 1.5 to about 3, or from about 1.5 to about 2.5, more preferably from about 1.5 to about 2 or from about 1.5 to about 1.75, most preferably from about 1.65 to about 1.75, or is about 1.65, about 1.7, or about 1.75.

In a still further example, the hair color altering composition may include from about 3% to about 10% of at least one alkoxylated fatty alcohol; from about 0.5% to about 1.75% of at least one fatty acid; at least about 3% of at least one fatty alcohol other than the alkoxylated fatty alcohol; from about 1% to about 1.5% of ammonium hydroxide; from about 0.03% to about 0.75% of ammonium bicarbonate; from about 0.03% to about 1% of monoethanolamine; at least one oxidizing component; at least one colorant compound chosen from oxidative dyes and precursors; and at least one thickening agent, wherein the molar ratio of ammonium hydroxide to ammonium bicarbonate is greater than about 1.5, for example ranges from about 1.5 to about 4, preferably from about 1.5 to about 3.75, from about 1.5 to about 3.5, from about 1.5 to about 3, or from about 1.5 to about 2.5, more preferably from about 1.5 to about 2 or from about 1.5 to about 1.75, most preferably from about 1.65 to about 1.75, or is about 1.65, about 1.7, or about 1.75.

As a further example, the hair color altering composition may include from about 18% to about 22% of at least one alkoxylated fatty alcohol; from about 2% to about 5% of at least one fatty acid; at least about 10% of at least one fatty alcohol other than the alkoxylated fatty alcohol; from about 3% to about 4.5% of ammonium hydroxide; from about 0.5% to about 1.5% of ammonium bicarbonate; from about 0.5% to about 2% of monoethanolamine; at least one oxidizing component; at least one colorant compound chosen from oxidative dyes and precursors; and at least one thickening agent, wherein the molar ratio of ammonium hydroxide to ammonium bicarbonate is greater than about 1.5, for example ranges from about 1.5 to about 4, preferably from about 1.5 to about 3.75, from about 1.5 to about 3.5, from about 1.5 to about 3, or from about 1.5 to about 2.5, more preferably from about 1.5 to about 2 or from about 1.5 to about 1.75, most preferably from about 1.65 to about 1.75, or is about 1.65, about 1.7, or about 1.75.

In a further example, the hair color altering composition may include from about 9% to about 11% of at least one alkoxylated fatty alcohol; from about 1% to about 2.5% of at least one fatty acid; at least about 5% of at least one fatty alcohol other than the alkoxylated fatty alcohol; from about 1.5% to about 2.25% of ammonium hydroxide; from about 0.25% to about 0.75% of ammonium bicarbonate; from about 0.25% to about 1% of monoethanolamine; at least one oxidizing component; at least one colorant compound chosen from oxidative dyes and precursors; and at least one thickening agent, wherein the molar ratio of ammonium hydroxide to ammonium bicarbonate is greater than about 1.5, for example ranges from about 1.5 to about 4, preferably from about 1.5 to about 3.75, from about 1.5 to about 3.5, from about 1.5 to about 3, or from about 1.5 to about 2.5, more preferably from about 1.5 to about 2 or from about 1.5 to about 1.75, most preferably from about 1.65 to about 1.75, or is about 1.65, about 1.7, or about 1.75.

In a still further example, the hair color altering composition may include from about 6% to about 7.5% of at least one alkoxylated fatty alcohol; from about 0.5% to about 1.75% of at least one fatty acid; at least about 3% of at least one fatty alcohol other than the alkoxylated fatty alcohol; from about 1% to about 1.5% of ammonium hydroxide; from about 0.1% to about 0.5% of ammonium bicarbonate; from about 0.1% to about 1% of monoethanolamine; at least one oxidizing component; at least one colorant compound chosen from oxidative dyes and precursors; and at least one thickening agent, wherein the molar ratio of ammonium hydroxide to ammonium bicarbonate is greater than about 1.5, for example ranges from about 1.5 to about 4, preferably from about 1.5 to about 3.75, from about 1.5 to about 3.5, from about 1.5 to about 3, or from about 1.5 to about 2.5, more preferably from about 1.5 to about 2 or from about 1.5 to about 1.75, most preferably from about 1.65 to about 1.75, or is about 1.65, about 1.7, or about 1.75.

Methods for Altering the Color of Hair

It has been surprisingly discovered that the application of the emulsion or cream hair color base and/or hair color composition onto keratin fibers such as hair unexpectedly results in satisfactory alteration of the color of the keratin fibers, while minimizing damage to the fibers compared to commercial or conventional hair color compositions which are typically left on the hair from 30 to 45 minutes or more. The coloring obtained using the compositions and process of the present disclosure may also be durable or wash/fade resistant.

The lifting of the color of the hair is evaluated by the tone height or level which describes the degree or level of lift or lightening. The tone heights range from 1 (black) to 10 (light blond), one unit corresponding to one tone; the higher the number, the lighter the shade or the greater the degree of lift.

It was surprisingly and unexpectedly discovered that by using the compositions and processes of the present disclosure on hair, the color of the hair was sufficiently lightened such that the degree of lift (increase in tone height) ranged from 0.5 to 4.5, such as up to 2, from 1 to 4, from 1.5 to 2.5, from 2 to 2.5, or about 2. For example, when the starting tone height before treating the hair is 5, and the tone height after treating the hair is 7.5, then the degree of lift or increase in tone height is 2.5. At the same time, the hair treated with the buffer systems or hair color bases and compositions did not feel as rough and did not visually appear to be as damaged as hair treated with conventional dyeing or lifting compositions, indicating less damage to the hair fiber compared to conventional hair coloring compositions, e.g. not comprising the hair color base or buffer systems according to the disclosure.

The hair color altering compositions described herein thus provide the performance of typical 35-minute or longer permanent cream hair color in less than about 25 minutes, for example less than about 20 minutes, or less than about 15 minutes, such as ranging from about 5 minutes to about 20 minutes or from about 10 minutes to about 15 minutes, for example about 10 minutes or about 15 minutes. Further, hair color altering compositions described herein provide a controlled reaction such that the risk of over processing result over the next five minutes after the 10 minutes or 15 minutes has evolved, to control or limit the continued evolution of hair color for 5 minutes after the processing period, thereby reducing processing time and minimizing damage to the hair, and overall minimizing other adverse effects.

As described above, an emulsion or cream hair color base may be mixed with an oxidizing component, e.g. at the time of or immediately before it is to be applied to the hair, such as up to about 30 minutes before, up to about 20 minutes before, or up to about 10 minutes before, for example about 1 to about 20 minutes before. The term "mixed" and all variations of this term as used herein refers to contacting or combining or reconstituting or dissolving or dispersing or blending or shaking the hair color base with the oxidizing component. It can also mean introducing the hair color base to the oxidizing component or vice versa. It may also mean placing the hair color base in the same vessel or container as the oxidizing component.

In some embodiments, an emulsion or cream hair color base according to the disclosure can be mixed or combined with an oxidizing component in a ratio by weight of from about 1:1 to about 1:10, such as from about 1:1 to about 1:4, such as from about 1:1 to about 1:3, or from about 1:1 to about 1:2, such as, for example about 1:1, about 1:2, about 1:3, or about 1:4.

Thus, methods or processes for lifting or altering the color of keratin fibers, in particular human hair, in accordance with the disclosure comprise contacting a hair color altering composition according to the disclosure with the keratin fibers such as hair.

In at least certain embodiments, the emulsion or cream hair color base and/or hair color altering composition may exhibit low odor, and/or may not have an unpleasant sensation on the scalp, and thus be more pleasant for the consumer. Additionally, the emulsion or cream hair color base and/or hair color altering composition may be easy to apply, for example with a standard bowl and brush or bottle.

Upon application of the hair color altering composition, and after an optional resting time (leave-on or "processing" time) on the hair, for example, ranging from about 1 to about 60 minutes, such as from about 5 to about 45 minutes, from about 5 to about 20 minutes, from about 10 to about 20 minutes, or about 20 minutes, the hair is rinsed. In various embodiments, it is not necessary to leave the hair color altering composition on the hair for longer than 30 minutes, and therefore in preferred embodiments the hair color altering composition is not left on the hair more than 25 minutes, for example not more than 20 minutes, not more than 15 minutes, or not more than 10 minutes. The hair may further be optionally washed with shampoo, rinsed again, optionally washed with a hair conditioning composition, and/or rinsed again, then dried. The shampoo and hair conditioning composition can be any conventional hair shampoo and conditioner products.

The temperature that the process of lifting or altering the color of hair is carried out at is generally between room temperature and 80° C., for example between room temperature and 60° C.

It has surprisingly been found that the emulsion or cream hair color altering compositions with buffer system described herein provide exceptional protection against over-processing and damage, equal to or greater than the protection against over-processing seen with hair color compositions with buffer system that are in liquid or gel form.

Thus, the disclosure further relates to methods for reducing damage to keratin fibers, for example hair, during a process for altering the color of the keratin fibers. The methods comprise applying to the keratin fibers a hair color altering composition according to the disclosure, and rinsing the hair color altering composition from the keratin fibers after a period of time no greater than 25 minutes after the hair color altering composition is applied to the keratin fibers, for example no greater than 20 minutes or no greater than 15 minutes. Optionally, the hair color altering composition may be rinsed from the keratin fibers in a timeframe of about 10 to about 15 minutes or about 10 to about 12 minutes after it is applied, or, for example, at about 10 minutes.

According to various embodiments, the process and compositions may be used on hair that has not been previously artificially dyed or pigmented. In further embodiments, the process and composition disclosed herein may be also used on hair that has been previously artificially dyed or pigmented.

Kits

A further embodiment of the disclosure includes hair dye kits or multi-compartment devices comprising one or more separate compartments or containers, wherein each compartment or container separately contains a buffer system, a hair color base, an oxidizing component, and optionally at least one additional composition.

For example, in one embodiment, a kit comprises (i) a first compartment containing an emulsion or cream hair color base according to the disclosure, and (ii) a second compartment containing one or more oxidizing components.

In yet another embodiment, a kit comprises (i) a first compartment containing an emulsion or cream hair color base according to the disclosure, (ii) a second compartment containing one or more oxidizing components, and (iii) a third compartment containing a composition comprising at least one component chosen from surfactants, fatty compounds, colorant compounds, solvents, or mixtures thereof.

Thus, the disclosure further relates to methods for preparing a composition for altering the color of keratin fibers, preferably hair, comprising mixing a hair color base according to the disclosure with an oxidizing component. In various embodiments, the hair color base may be mixed with an oxidizing composition comprising an oxidizing agent at a mixing ratio of hair color base:oxidizing composition of about 1:1, about 1:2, about 1:3, about 1:4, or about 1:5. It should be understood, however, that the oxidizing component and hair color base may be present together in a kit according to the disclosure, or may be separate, and methods of preparing a composition for altering the color of keratin fibers should not be limited only to kits according to the disclosure.

Having described the many embodiments of the present invention in detail, it will be apparent that modifications and variations are possible without departing from the scope of the disclosure defined in the appended claims. Furthermore, it should be appreciated that all examples in the present disclosure, while illustrating many embodiments of the disclosure, are provided as non-limiting examples and are, therefore, not to be taken as limiting the various aspects so illustrated. It is to be understood that all definitions herein are provided for the present disclosure only.

In this application, the use of the singular includes the plural unless specifically stated otherwise. The singular forms "a," "an," "the," and "at least one" are understood to encompass the plural as well as the singular unless the context clearly dictates otherwise. The expression "one or more" means "at least one" and thus includes individual components as well as mixtures/combinations. Likewise, the term "a" should be understood as "at least one," "one or more," etc., unless expressly stated otherwise. For example "a salt" also means "at least one salt," "one or more salts,"

"salts," etc. Thus, where the disclosure refers to "an element selected from the group consisting of A, B, C, D, E, F, a salt thereof, or a mixture thereof," it indicates that one or more of A, B, C, D, and F may be included, one or more of a salt of A, a salt of B, a salt of C, a salt of D, a salt of E, and a salt of F may be included, or a mixture of any two or more of A, B, C, D, E, F, a salt of A, a salt of B, a salt of C, a salt of D, a salt of E, and a salt of F may be included.

As used herein, the phrases "and mixtures thereof," "and a mixture thereof," "and combinations thereof," "and a combination thereof," "or mixtures thereof," "or a mixture thereof," "or combinations thereof," "or a combination thereof," and variations thereof are used interchangeably to denote that the listing of components immediately preceding the phrase, such as "A, B, C, D, or mixtures thereof" signify that the component(s) may be chosen from A, from B, from C, from D, from A+B, from A+B+C, from A+D, from A+C+D, etc., without limitation on the variations thereof. Thus, the components may be used individually or in any combination thereof.

All amounts given herein are relative to the amount of active material, unless otherwise indicated.

Whether or not expressly stated, all percentages, parts and ratios herein are based upon the total weight of the composition in which it is present, e.g. the hair base composition, the oxidizing composition, the hair color altering composition, unless otherwise indicated.

Other than in the operating examples, or where otherwise indicated, all numbers expressing quantities of components and/or reaction conditions are to be understood as being modified in all instances by the term "about" whether or not so stated. Similarly, a range given of "about 1% to 10%" is intended to have the term "about" modifying both the 1% and the 10% endpoints. As used herein, "about" is understood to encompass ±10%, ±9%, ±8%, ±7%, ±6%, ±5%, ±4%, ±3%, ±2%, ±1%, ±0.5%, ±0.1%, or ±0.01%. All numbers expressing quantities of components are given by weight, relative to the total weight of the composition in which the component is present, unless otherwise indicated.

All ranges and amounts given herein are intended to include sub-ranges and amounts using any disclosed point as an end point. Thus, a range from 1-5, includes specifically 1, 2, 3, 4, and 5, as well as sub ranges such as 2-5, 3-5, 2-3, 2-4, 1-4, etc. All ranges and values disclosed herein are inclusive and combinable. Further, it is expressly contemplated that any value or point reported in the Examples that falls within a range described herein can serve as a minimum or maximum value to derive a sub-range.

As used herein, the expressions "ranging from" and "between" are inclusive of the endpoints of the recited range(s).

As used herein, if a component is described as being present "in an amount up to" a certain amount, it is intended that such component is, in fact, present in the composition, i.e. is present in an amount greater than 0%.

The term "and/or" should be understood to include both the conjunctive and the disjunctive and expressly covers instances of either without reference to the other. For example, "a colorant chosen from pigments and/or dyes" includes a colorant chosen from pigments and dyes, as well as a colorant chosen from pigments or dyes.

"Keratin fibers" include, but are not limited to, human hair. In one specific embodiment, the terms "keratin fibers," "hair," and the like exclude eyelashes, eyebrows, facial hair, and/or any other hair besides hair on the scalp of the head.

As used herein, the term "substantially free" or "essentially free" means the specific material may be present in small amounts that do not materially affect the basic and novel characteristics of the compositions according to the disclosure. For instance, there may be less than 2% by weight of a specific material added to a composition, based on the total weight of the compositions (provided that an amount of less than 2% by weight does not materially affect the basic and novel characteristics of the compositions according to the disclosure. Similarly, the compositions may include less than 2%, less than 1.5%, less than 1%, less than 0.5%, less than 0.1%, less than 0.05%, or less than 0.01%, or none of the specified material. Furthermore, all components that are positively set forth in the instant disclosure may be negatively excluded from the claims, e.g., a claimed composition may be "free," "essentially free" (or "substantially free") of one or more components that are positively set forth in the instant disclosure. The term "substantially free" or "essentially free" as used herein may also mean that the specific material is not added to the composition but may still be present in small quantities in a raw material that is included in the composition.

The term "substantially anhydrous" as used herein means that the referenced composition is free or substantially free of water, for example, no more than 5% by weight, or no more than 2% by weight, or no more than 1% by weight, based on the weight of the oxidizing composition. It should be noted that this refers for example to bound water, such as the water of crystallization of the salts or traces of water absorbed by the raw materials used in the preparation of the compositions according to the disclosure. In some embodiments, the phrases "anhydrous or substantially anhydrous," or "free or substantially free of water," mean that the composition has no added water, but small or very small amounts of water may be present as a residual constituent of the various component(s) added to the compositions.

All numbers expressing pH values are to be understood as being modified by the term "about," and as encompassing readings using a pH meter having a variation of up to ±10%, such as up to ±9%, up to ±8%, up to ±7%, up to ±6%, up to ±5%, up to ±4%, up to ±3%, up to ±2%, or up to ±1%, which a skilled person will recognize relates to the inherent variation in pH meters.

The term "altering the color" or "color-altering" as used herein may refer lifting or lightening the color of hair. It can also refer to dyeing or coloring hair or depositing color onto the hair. In certain instances, it refers to lifting or lightening the color of hair and depositing color onto the hair at the same time.

"Formed from," as used herein, means obtained from chemical reaction of, wherein "chemical reaction," includes spontaneous chemical reactions and induced chemical reactions. As used herein, the phrase "formed from", is open ended and does not limit the components of the composition to those listed, e.g., as component (i) and component (ii). Furthermore, the phrase "formed from" does not limit the order of adding components to the composition or require that the listed components (e.g., components (i) and (ii)) be added to the composition before any other components.

"Hydrocarbons," as used herein, include alkanes, alkenes, and alkynes, wherein the alkanes comprise at least one carbon, and the alkenes and alkynes each comprise at least two carbons; further wherein the hydrocarbons may be chosen from linear hydrocarbons, branched hydrocarbons, and cyclic hydrocarbons; further wherein the hydrocarbons may optionally be substituted; and further wherein the hydrocarbons may optionally further comprise at least one heteroatom intercalated in the hydrocarbon chain.

"Silicone compound," as used herein, includes, for example, silica, silanes, silazanes, siloxanes, and organosiloxanes; and refers to a compound comprising at least one silicon; wherein the silicone compound may be chosen from linear silicone compounds, branched silicone compounds, and cyclic silicone compounds; further wherein the silicone compound may optionally be substituted; and further wherein the silicone compound may optionally further comprise at least one heteroatom intercalated in the silicone chain, wherein the at least one heteroatom is different from the at least one silicon.

"Substituted," as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Polymers," as defined herein, include homopolymers and copolymers formed from at least two different types of monomers.

The terms "rheology modifier," "thickener," "thickening agent," and the like are used interchangeably herein without intending to be limiting, unless otherwise noted.

Where an acid is disclosed as useful according to embodiments of the disclosure, it is expressly contemplated that salts of the acid are included; for example, disclosure of "citric acid" includes "salts of citric acid." Further, the term "salts" as used herein may include salts having a counterion such as an alkali metal, alkaline earth metal, or ammonium counterion. This list of counterions, however, is non-limiting. Salts also include a dissociated form of a compound, e.g. in an aqueous solution.

As used herein, the terms "applying a composition onto keratin materials," "applying a composition onto hair," and variations of these phrases are intended to mean contacting the keratin materials including hair and skin, with at least one of the compositions of the disclosure, in any manner. It may also mean contacting the keratin materials in an effective amount.

Unless otherwise expressly stated, it is in no way intended that any method set forth herein be construed as requiring that its steps be performed in a specific order. Accordingly, where a method claim does not expressly recite an order to be followed by its steps or it is not otherwise specifically stated in the claims or descriptions that the steps are to be limited to a specific order, it is no way intended that any particular order be inferred.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

The examples that follow serve to illustrate embodiments of the present disclosure without, however, being limiting in nature.

EXAMPLES

Implementation of the present disclosure is demonstrated by way of the following non-limiting examples.

In the Examples below, all amounts are given in percent by weight of active material, relative to the total weight of the composition in which they are present.

EXAMPLE 1

Inventive Hair Color Base Compositions

Inventive hair color base compositions having the components (and amounts thereof) found in Table 1A were prepared, with each of hair color bases 1A-1T having the specific colorants in Table 1 B included in the amounts indicated. Each of the hair color base compositions was in emulsion or cream form, and had a pH greater than 8.5.

TABLE 1A

| HAIR COLOR BASE | |
|---|---|
| Component | Amount |
| Ammonium bicarbonate | 0.99 |
| Ammonium hydroxide | 3.89 |
| Ammonium thiolactate | 0.46 |
| Ethanolamine | 1.35 |
| Glycol distearate | 2.0 |
| Cetearyl alcohol | 11.5 |
| Lauric acid | 3.0 |
| Deceth-3 | 9.0 |
| Laureth-12 | 7.0 |
| Oleth-30 | 4.0 |
| Polymer/thickening agent | 4.2 |
| Colorants | See Table 1B |
| Additives (fragrance, preservatives, pH adjusters, amino acids, vitamins, chelators, emollients, antistatic agents) | ≤5 |
| Solvents (water, non-aqueous solvents) | QS 100 |

TABLE 1B

| COLORANTS/AMOUNTS IN HAIR COLOR BASE COMPOSITIONS | | |
|---|---|---|
| Example | Colorant Amount | Colorant |
| 1A | 5.6 | HYDROXYBENZOMORPHOLINE; 2,4-DIAMINOPHENOXYETHANOL HCl; 6-HYDROXYINDOLE; TITANIUM DIOXIDE; N,N-BIS(2-HYDROXYETHYL)-p-PHENYLENEDIAMINE SULFATE; m-AMINOPHENOL; p-PHENYLENEDIAMINE; p-AMINOPHENOL |
| 1B | 4.8 | HYDROXYBENZOMORPHOLINE; 2,4-DIAMINOPHENOXYETHANOL HCl; 6-HYDROXYINDOLE; TITANIUM DIOXIDE; N,N-BIS(2-HYDROXYETHYL)-p-PHENYLENEDIAMINE SULFATE; m-AMINOPHENOL; p-PHENYLENEDIAMINE |

TABLE 1B-continued

COLORANTS/AMOUNTS IN HAIR COLOR BASE COMPOSITIONS

| Example | Colorant Amount | Colorant |
|---|---|---|
| 1C | 3.9 | HYDROXYBENZOMORPHOLINE; 2,4-DIAMINOPHENOXYETHANOL HCl; 6-HYDROXYINDOLE; TITANIUM DIOXIDE; N,N-BIS(2-HYDROXYETHYL)-p-PHENYLENEDIAMINE SULFATE; 2-AMINO-3-HYDROXYPYRIDINE; m-AMINOPHENOL; p-PHENYLENEDIAMINE |
| 1D | 4.8 | TOLUENE-2,5-DIAMINE; HYDROXYBENZOMORPHOLINE; 2,4-DIAMINOPHENOXYETHANOL HCl; 6-HYDROXYINDOLE; TITANIUM DIOXIDE; N,N-BIS(2-HYDROXYETHYL)-p-PHENYLENEDIAMINE SULFATE; 2-AMINO-3-HYDROXYPYRIDINE; m-AMINOPHENOL |
| 1E | 4.3 | TOLUENE-2,5-DIAMINE; HYDROXYBENZOMORPHOLINE; 2,4-DIAMINOPHENOXYETHANOL HCl; 6-HYDROXYINDOLE; TITANIUM DIOXIDE; N,N-BIS(2-HYDROXYETHYL)-p-PHENYLENEDIAMINE SULFATE; 2-AMINO-3-HYDROXYPYRIDINE; m-AMINOPHENOL |
| 1F | 4.0 | TOLUENE-2,5-DIAMINE; HYDROXYBENZOMORPHOLINE; 2,4-DIAMINOPHENOXYETHANOL HCl; 6-HYDROXYINDOLE; TITANIUM DIOXIDE; N,N-BIS(2-HYDROXYETHYL)-p-PHENYLENEDIAMINE SULFATE; 2-AMINO-3-HYDROXYPYRIDINE; m-AMINOPHENOL |
| 1G | 2.2 | TOLUENE-2,5-DIAMINE; HYDROXYBENZOMORPHOLINE; 2,4-DIAMINOPHENOXYETHANOL HCl; 6-HYDROXYINDOLE; TITANIUM DIOXIDE; N,N-BIS(2-HYDROXYETHYL)-p-PHENYLENEDIAMINE SULFATE; 2-AMINO-3-HYDROXYPYRIDINE; m-AMINOPHENOL |
| 1H | 2.5 | TOLUENE-2,5-DIAMINE; HYDROXYBENZOMORPHOLINE; 2,4-DIAMINOPHENOXYETHANOL HCl; 6-HYDROXYINDOLE; TITANIUM DIOXIDE; N,N-BIS(2-HYDROXYETHYL)-p-PHENYLENEDIAMINE SULFATE; 2-AMINO-3-HYDROXYPYRIDINE; m-AMINOPHENOL |
| 1I | 2.7 | TOLUENE-2,5-DIAMINE; HYDROXYBENZOMORPHOLINE; 2,4-DIAMINOPHENOXYETHANOL HCl; 6-HYDROXYINDOLE; TITANIUM DIOXIDE; N,N-BIS(2-HYDROXYETHYL)-p-PHENYLENEDIAMINE SULFATE; 2-AMINO-3-HYDROXYPYRIDINE; m-AMINOPHENOL |
| 1J | 1.1 | TOLUENE-2,5-DIAMINE; HYDROXYBENZOMORPHOLINE; 2,4-DIAMINOPHENOXYETHANOL HCl; 6-HYDROXYINDOLE; TITANIUM DIOXIDE; N,N-BIS(2-HYDROXYETHYL)-p-PHENYLENEDIAMINE SULFATE; 2-AMINO-3-HYDROXYPYRIDINE; m-AMINOPHENOL |
| 1K | 1.3 | TOLUENE-2,5-DIAMINE; HYDROXYBENZOMORPHOLINE; 2,4-DIAMINOPHENOXYETHANOL HCl; 6-HYDROXYINDOLE; TITANIUM DIOXIDE; N,N-BIS(2-HYDROXYETHYL)-p-PHENYLENEDIAMINE SULFATE; 2-AMINO-3-HYDROXYPYRIDINE; m-AMINOPHENOL |
| 1L | 0.76 | TOLUENE-2,5-DIAMINE; HYDROXYBENZOMORPHOLINE; 2,4-DIAMINOPHENOXYETHANOL HCl; 6-HYDROXYINDOLE; TITANIUM DIOXIDE; N,N-BIS(2-HYDROXYETHYL)-p-PHENYLENEDIAMINE SULFATE; 2-AMINO-3-HYDROXYPYRIDINE; m-AMINOPHENOL |
| 1M | 1.0 | TOLUENE-2,5-DIAMINE; HYDROXYBENZOMORPHOLINE; 2,4-DIAMINOPHENOXYETHANOL HCl; 6-HYDROXYINDOLE; TITANIUM DIOXIDE; N,N-BIS(2-HYDROXYETHYL)-p-PHENYLENEDIAMINE SULFATE; 2-AMINO-3-HYDROXYPYRIDINE; m-AMINOPHENOL |
| 1N | 0.76 | TOLUENE-2,5-DIAMINE; HYDROXYBENZOMORPHOLINE; 2,4-DIAMINOPHENOXYETHANOL HCl; 6-HYDROXYINDOLE; TITANIUM DIOXIDE; N,N-BIS(2-HYDROXYETHYL)-p-PHENYLENEDIAMINE SULFATE; 2-AMINO-3-HYDROXYPYRIDINE; m-AMINOPHENOL |
| 1O | 5.6 | HYDROXYBENZOMORPHOLINE; 2,4-DIAMINOPHENOXYETHANOL HCl; 6-HYDROXYINDOLE; TITANIUM DIOXIDE; N,N-BIS(2-HYDR0XYETHYL)-p-PHENYLENEDIAMINE SULFATE; m-AMINOPHENOL; p-PHENYLENEDIAMINE; p-AMINOPHENOL |
| 1P | 4.8 | TOLUENE-2,5-DIAMINE; HYDROXYBENZOMORPHOLINE; 2,4-DIAMINOPHENOXYETHANOL HCl; 6-HYDROXYINDOLE; TITANIUM DIOXIDE; N,N-BIS(2-HYDROXYETHYL)-p-PHENYLENEDIAMINE SULFATE; 2-AMINO-3-HYDROXYPYRIDINE; m-AMINOPHENOL |

TABLE 1B-continued

COLORANTS/AMOUNTS IN HAIR COLOR BASE COMPOSITIONS

| Example | Colorant Amount | Colorant |
|---|---|---|
| 1Q | 2.1 | TOLUENE-2,5-DIAMINE; HYDROXYBENZOMORPHOLINE; 2,4-DIAMINOPHENOXYETHANOL HCl; 6-HYDROXYINDOLE; TITANIUM DIOXIDE; N,N-BIS(2-HYDROXYETHYL)-p-PHENYLENEDIAMINE SULFATE; 2-AMINO-3-HYDROXYPYRIDINE; m-AMINOPHENOL |
| 1R | 5.6 | HYDROXYBENZOMORPHOLINE; 2,4-DIAMINOPHENOXYETHANOL HCl; 6-HYDROXYINDOLE; TITANIUM DIOXIDE m-AMINOPHENOL; p-PHENYLENEDIAMINE; p-AMINOPHENOL |
| 1S | 4.8 | TOLUENE-2,5-DIAMINE; HYDROXYBENZOMORPHOLINE; 2,4-DIAMINOPHENOXYETHANOL HCl; 6-HYDROXYINDOLE; TITANIUM DIOXIDE; N,N-BIS(2-HYDROXYETHYL)-p-PHENYLENEDIAMINE SULFATE; 2-AMINO-3-HYDROXYPYRIDINE; m-AMINOPHENOL |
| 1T | 2.1 | TOLUENE-2,5-DIAMINE; HYDROXYBENZOMORPHOLINE; 2,4-DIAMINOPHENOXYETHANOL HCl; 6-HYDROXYINDOLE; TITANIUM DIOXIDE; N,N-BIS(2-HYDROXYETHYL)-p-PHENYLENEDIAMINE SULFATE; 2-AMINO-3-HYDROXYPYRIDINE; m-AMINOPHENOL |

EXAMPLE 2

Inventive Hair Color Altering Compositions

Inventive hair color altering compositions 1A'-1T' were prepared by mixing equal amounts (1:1 mixing ratio) of each of hair color base compositions 1A-1T with an aqueous 20 V hydrogen peroxide oxidizing composition (developer). The pH of each of hair color altering composition 1A'-1T' (mixture prepared from mixing inventive hair color base composition plus 20 V developer) was greater than 7.

Each hair color altering composition (mixture) was applied to two swatches of hair and allowed to process under ambient conditions for either 10 minutes or 15 minutes, after which the swatches of hair were rinsed, shampooed, rinsed again, and allowed to dry. Once dry, the color imparted to the hair was visually evaluated. All swatches demonstrated acceptable alteration of the color from the initial swatch color. Additionally, it was observed that the swatches that were processed for 15 minutes did not exhibit damage typically associated with over processing.

The above Examples demonstrate that hair color altering compositions comprising an emulsion or cream hair color base according to the disclosure, result in faster processing time and more controlled reaction, with comparable or improved alteration of hair color. Faster processing time and more controlled reaction contribute to less damage and more controlled color deposition/lightening, thereby reducing the risk of over processing and damaging the hair.

It will be apparent to those skilled in the art that various modifications and variations can be made in the delivery system, composition and methods of the invention without departing from the spirit or scope of the invention.

The invention claimed is:

1. A hair color base in the form of a cream or an emulsion comprising:
   (a) about 10% to about 30% of alkoxylated fatty alcohols;
   (b) about 1% to about 8% of fatty acids;
   (c) at least about 8% of fatty alcohols other than alkoxylated fatty alcohols; and
   (d) a buffer system comprising:
      (i) about 0.1% to about 10% ammonium hydroxide;
      (ii) about 0.1% to about 5% ammonium bicarbonate; and
      (iii) optionally, about 0.5% to about 5% of monoethanolamine;
   wherein the molar ratio of ammonium hydroxide to ammonium bicarbonate is at least about 1.2, and
   wherein all amounts are by weight, based on the total weight of the hair color base.

2. The hair color base according to claim 1, further comprising at least one additional component chosen from thickeners, colorant compounds, or mixtures thereof.

3. The hair color base according to claim 1, wherein the molar ratio of ammonium hydroxide to ammonium bicarbonate ranges from about 1.2 to about 3.75.

4. The hair color base according to claim 1, wherein the buffer system comprises:
   (i) about 3.5% to about 4.25% of ammonium hydroxide,
   (ii) about 0.5% to about 1.5% ammonium bicarbonate, and
   (iii) about 0.5% to about 1.5% of monoethanolamine,
   wherein all amounts are by weight, based on the total weight of the hair color base.

5. The hair color base according to claim 3, wherein the molar ratio of ammonium hydroxide to ammonium bicarbonate ranges from about 1.5 to about 2.5.

6. The hair color base according to claim 1, wherein the amount by weight of ammonium hydroxide is greater than the amount by weight of ammonium bicarbonate.

7. The hair color base according to claim 1, comprising:
   (a) about 18% to about 25% of alkoxylated fatty alcohols;
   (b) about 2% to about 6% of fatty acids;
   (c) about 8% to about 20% of fatty alcohols other than alkoxylated fatty alcohols; and
   (d) a buffer system comprising:
      (i) about 2% to about 5% ammonium hydroxide;
      (ii) about 0.1% to about 2.5% ammonium bicarbonate; and
      (iii) about 0.75% to about 3% of monoethanolamine;
   wherein the molar ratio of ammonium hydroxide to ammonium bicarbonate ranges from about 1.5 to about 2.5, and
   wherein all amounts are by weight, based on the total weight of the hair color base.

8. A hair color altering composition comprising a hair color base in the form of a cream or an emulsion comprising:
(a) about 2% to about 30% of alkoxylated fatty alcohols;
(b) about 0.2% to about 8% of fatty acids;
(c) at least about 2% of fatty alcohols other than alkoxylated fatty alcohols; and
(d) a buffer system comprising:
(i) about 0.02% to about 10% ammonium hydroxide;
(ii) about 0.02% to about 5% ammonium bicarbonate; and
(iii) about 0.05% to about 5% of monoethanolamine; and
(e) at least one colorant component chosen from oxidation dye precursors or direct dyes;
wherein the molar ratio of ammonium hydroxide to ammonium bicarbonate is at least about 1.5; and
wherein all amounts are by weight, based on the total weight of the hair color altering composition.

9. The hair color altering composition according to claim 8, further comprising at least one oxidizing component.

10. The hair color altering composition according to claim 9, wherein the oxidizing component comprises hydrogen peroxide.

11. The hair color altering composition according to claim 8, wherein the buffer system comprises from about 1% to about 6% ammonium hydroxide, about 0.25% to about 2.5% ammonium bicarbonate, and about 0.5% to about 2.5% monoethanolamine.

12. The hair color altering composition according to claim 8, wherein the molar ratio of ammonium hydroxide to ammonium bicarbonate is at least about 1.65.

13. The hair color altering composition according to claim 8, further comprising at least one additional component selected from thickeners, solvents, fatty substances, cationic polymers, surfactants, conditioning agents, antioxidants, pH adjusters, antistatic agents, vitamins, fillers, or mixtures of two or more thereof.

14. The hair color altering composition according to claim 8, further comprising an oxidizing agent, comprising:
(a) about 5% to about 15% of alkoxylated fatty alcohols;
(b) about 0.5% to about 4% of fatty acids;
(c) about 5% to about 10% of fatty alcohols other than alkoxylated fatty alcohols;
(d) a buffer system comprising
(i) about 0.05% to about 5% ammonium hydroxide;
(ii) about 0.05% to about 2.5% ammonium bicarbonate; and
(iii) about 0.25% to about 2.5% of monoethanolamine,
wherein the at least one colorant compound is chosen from oxidation dye precursors,
wherein the molar ratio of ammonium hydroxide to ammonium bicarbonate ranges from about 1.5 to about 3, and
wherein all amounts are by weight, based on the total weight of the hair color altering composition.

15. The hair color altering composition according to claim 14, wherein the oxidizing agent is hydrogen peroxide.

16. The hair color altering composition according to claim 8, comprising from about 1% to about 2.5% of ammonium hydroxide, about 0.25% to about 1% ammonium bicarbonate, and about 0.25% to about 1.5% of monoethanolamine, and wherein the molar ratio of ammonium hydroxide to ammonium bicarbonate ranges from about 1.5 to about 2.5.

17. A method for altering the color of the keratin fibers, comprising applying to the keratin fibers a color-altering composition in the form of a cream or an emulsion comprising:
(a) about 2% to about 30% of alkoxylated fatty alcohols;
(b) about 0.2% to about 8% of fatty acids;
(c) at least about 2% of fatty alcohols other than alkoxylated fatty alcohols;
(d) a buffer system comprising:
(i) about 0.02% to about 10% ammonium hydroxide;
(ii) about 0.02% to about 5% ammonium bicarbonate; and
(iii) about 0.05% to about 5% of monoethanolamine; and
(e) at least one colorant component selected from oxidation dye precursors or direct dyes;
wherein the molar ratio of ammonium hydroxide to ammonium bicarbonate is at least about 1.2, and
wherein all amounts are by weight, based on the total weight of the hair color altering composition.

18. The method according to claim 17, further comprising rinsing the hair color altering composition from the keratin fibers after a period of time ranging from about 5 to about 20 minutes after the hair color altering composition is applied to the keratin fibers.

19. A method for preparing a composition for altering the color of keratin fibers comprising mixing a hair color base in the form of a cream or an emulsion with an oxidizing component, wherein the hair color base comprises:
(a) about 10% to about 30% of alkoxylated fatty alcohols;
(b) about 1% to about 8% of fatty acids;
(c) at least about 8% of fatty alcohols other than alkoxylated fatty alcohols;
(d) a buffer system comprising:
(i) about 0.1% to about 10% ammonium hydroxide;
(ii) about 0.1% to about 5% ammonium bicarbonate; and
(iii) about 0.5% to about 5% of monoethanolamine; and
(e) a colorant component chosen from oxidative dye precursors or direct dyes,
wherein the molar ratio of ammonium hydroxide to ammonium bicarbonate is at least about 1.2, and
wherein all amounts are by weight, based on the total weight of the composition for altering the color of keratin fibers.

20. The method according to claim 19, wherein the hair color base is mixed with the oxidizing component in a ratio of hair color base:oxidizing component ranging from about 1:1 to about 1:4.

21. The method according to claim 19, wherein the oxidizing component comprises hydrogen peroxide.

* * * * *